US006200771B1

(12) United States Patent
Liu et al.

(10) Patent No.: US 6,200,771 B1
(45) Date of Patent: *Mar. 13, 2001

(54) METHOD OF USING A NOVEL PHOSPHODIESTERASE IN PHARMACEUTICAL SCREEING TO IDENTIFY COMPOUNDS FOR TREATMENT OF NEOPLASIA

(75) Inventors: Li Liu, Northwales; Rifat Pamukcu, Spring House; W. Joseph Thompson; Gary A. Piazza, both of Doylestown; Han Li, Yardley, all of PA (US); Bing Zhu, Mobile, AL (US)

(73) Assignee: Cell Pathways, Inc., Hosham, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,375

(22) Filed: Oct. 15, 1998

(51) Int. Cl.[7] ....................................................... C12Q 1/44
(52) U.S. Cl. ................................. 435/19; 435/25; 435/184
(58) Field of Search .............................. 435/4, 6, 15, 19, 435/184, 196, 25; 424/9.1, 9.2; 436/64

(56) References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,076,711 | 2/1978 | Ganguly et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,457,927 | 7/1984 | Biere et al. . |
| 4,460,590 | 7/1984 | Möller . |
| 4,460,591 | 7/1984 | DeGraw et al. . |
| 4,880,810 | 11/1989 | Lowe, III et al. . |
| 4,885,301 | 12/1989 | Coates . |
| 4,923,874 | 5/1990 | McMahon et al. . |
| 4,971,972 | 11/1990 | Doll et al. . |

(List continued on next page.)

FOREIGN PATENT DOCUMENTS

| | | |
|---|---|---|
| 3038166 | 6/1981 | (DE) . |
| 274218 | 12/1989 | (DE) . |
| 0 330 004 A1 | 6/1989 | (EP) . |
| 0 347146 A2 | 12/1989 | (EP) . |
| 0 349239 A2 | 1/1990 | (EP) . |
| 0 351058 | 1/1990 | (EP) . |
| 0 352960 A2 | 1/1990 | (EP) . |

(List continued on next page.)

OTHER PUBLICATIONS

Curtis–Prior P., Cyclic Nucleotide Phosphodiesterase Activity of Human Normal and Carcinomatous Lung Tissue, The Lancet p. 1224, Dec. 1976.*

Jiang X. Inhibition of Calmodulin Dependent Phosphodiesterase Induces Apoptosis in Human Leukemic Cells. Proc Natl Acad Sci (USA) 93, pp. 11236–11241, Oct. 1996.*

Blaya C., Effect of the Protein Kinase Inhbitors. European J of Pharmcology 354, 99–104, Jul. 1998.*

Earnest D., Piroxicam and Other Cyclooxygenase Inhibitors: Potential for Cancer Chemoprevention. J of Cellular Biochemistry Supp. 161:156–166, 1992.*

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

(List continued on next page.)

*Primary Examiner*—Ralph Gitomer
(74) *Attorney, Agent, or Firm*—Robert W. Stevenson

(57) ABSTRACT

A method for identifying compounds useful for the treatment of neoplasia involves acertaining whether such compounds exhibit an ability to inhibit a PDE that is characterized by cGMP specificity, cooperative kinetic behavior and insensitivity to phosphorylation.

13 Claims, 15 Drawing Sheets

U.S. PATENT DOCUMENTS

| | | |
|---|---|---|
| 5,073,559 | 12/1991 | Coates . |
| 5,091,431 | 2/1992 | Tulshian et al. . |
| 5,147,875 | 9/1992 | Coates et al. . |
| 5,175,151 | 12/1992 | Afonso et al. . |
| 5,223,501 | 6/1993 | Chakravarty et al. . |
| 5,250,535 | 10/1993 | Verheyden et al. . |
| 5,254,571 | 10/1993 | Coates et al. . |
| 5,358,952 | 10/1994 | Moschel et al. . |
| 5,376,683 | 12/1994 | Klar et al. . |
| 5,393,755 | 2/1995 | Neustadt et al. . |
| 5,401,774 | 3/1995 | Pamukcu et al. . |
| 5,439,895 | 8/1995 | Lee et al. . |
| 5,488,055 | 1/1996 | Kumar et al. . |
| 5,614,530 | 3/1997 | Kumar et al. . |
| 5,614,627 | 3/1997 | Takase et al. . |
| 5,728,563 | 3/1998 | Toshio . |
| 5,747,506 * | 5/1998 | Naef ................................ 514/307 |
| 5,756,818 | 5/1998 | Buchmann et al. . |
| 5,858,694 * | 1/1999 | Piazza et al. ........................ 435/19 |

FOREIGN PATENT DOCUMENTS

| | | |
|---|---|---|
| 0 395328 A2 | 10/1990 | (EP) . |
| 0 428268 A2 | 5/1991 | (EP) . |
| 0 463756 A1 | 1/1992 | (EP) . |
| 0 485157 A2 | 5/1992 | (EP) . |
| 0 485158 A2 | 5/1992 | (EP) . |
| 0 485171 A2 | 5/1992 | (EP) . |
| 0 485172 A2 | 5/1992 | (EP) . |
| 0 485173 A2 | 5/1992 | (EP) . |
| 0 508586 A1 | 10/1992 | (EP) . |
| 0 526004 A1 | 2/1993 | (EP) . |
| 0 607439 A1 | 7/1994 | (EP) . |
| 0 722937 A1 | 7/1996 | (EP) . |
| 0 743304 A1 | 10/1996 | (EP) . |
| 807826 | 1/1959 | (GB) . |
| 2063249 | 6/1981 | (GB) . |
| 56-53659 | 5/1981 | (JP) . |
| 57-167974 | 10/1982 | (JP) . |
| 8-311035 | 11/1996 | (JP) . |
| WO 92/03419 | 3/1992 | (WO) . |
| WO 93/07149 | 4/1993 | (WO) . |
| WO 93/12095 | 6/1993 | (WO) . |
| WO 94/05661 | 3/1994 | (WO) . |
| WO 94/19351 | 9/1994 | (WO) . |
| WO 94/29277 | 12/1994 | (WO) . |
| WO 95 18969 | 7/1995 | (WO) . |
| WO 95/26743 | 10/1995 | (WO) . |
| WO 97/03070 | 1/1997 | (WO) . |
| WO 97/03985 | 2/1997 | (WO) . |
| WO 97/24334 | 7/1997 | (WO) . |
| WO 98/14448 | 4/1998 | (WO) . |
| WO 98/15530 | 4/1998 | (WO) . |
| WO 98/16224 | 4/1998 | (WO) . |
| WO 98/16521 | 4/1998 | (WO) . |
| WO 98/17668 | 4/1998 | (WO) . |
| WO 98/08848 | 5/1998 | (WO) . |
| WO 98/23597 | 6/1998 | (WO) . |
| WO 98/38168 | 9/1998 | (WO) . |
| WO 96/32379 | 10/1998 | (WO) . |

OTHER PUBLICATIONS

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'-Monophosphate and Guanosine Cyclic 3',5'-Monophosphate Phosphodiesterases, Molecular Pharmacology, 13, pp. 38–43 (1976).

Drees, Markus et al., 3',5'-Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Ho–Sam Ahn et al., Potent Tetracyclic Guanine Inhibitors of PDE1 and PDE5 Cyclic Guanosine Monophosphate Phosphodiesterases with Oral Antihypertensive Activity: J. Med. Chem. 1997, 40, pp. 2196–2210.

J.A. Mitchell et al., Selectivity of nonsteroidal antiinflammatory drugs as inhibitors of constitutive and inducible cyclooxygenase; Proc. Natl. Acad. Sci. USA, vol. 90, Dec. 1994, pp 11693–11697.

J.D. Gaffen et al.: Increased killing of malignant cells by giving indomethacin with methotrexate, p. 30; column 1; XP002084860Chemical Abstract, vol. 106, No. 11, Mar. 16, 1987, abstract No. 78377, J.D.

Tsou, K–C. et al. 5'–Nucleotide Phosphodiesterase Isozyme–V as a Marker for Liver Metastases in Breast Cancer Patients, Cancer 54:1788–1793, 1984.

Epstein, P.M. et al. Increased Cyclic Nucleotide Phospho Di Esterase Activity Associated with Proliferation and Cancer in Human Murine Lymphoid Cells. Dep. Pharmacol., Univ. Tex. Med. Sch., M.D. Anderson Hospital, Houston, Tex. 77030, USA. Biosis: 78:140912 Abstract.

* cited by examiner

METHOD OF USING A NOVEL PHOSPHODIESTERASE IN PHARMACEUTICAL SCREEING TO IDENTIFY COMPOUNDS FOR TREATMENT OF NEOPLASIA

BACKGROUND OF THE INVENTION

This invention relates to a novel cGMP-specific phosphodiesterase that provides a method for identifying compounds potentially useful for the treatment and prevention of pre-cancerous and cancerous lesions in mammals.

Cancer and precancer research is replete with publications that describe various biochemical molecules that are over-expressed in neoplastic tissue, leading one research group after another to research whether specfic over-expressed molecules are responsible for the disease, and whether, if the over-expression were inhibited, neoplasia could be alleviated. For example, in familial adenomatous polyposis ("FAP"), Waddell in 1983 (Waddell, W. R. et al., "Sulindac for Polyposis of the Colon," *Journal of Surgical Oncology*, 24:83–87, 1983) hypothesized that since prostaglandins were over-expressed in such polyps, non-steroidal anti-inflammatory drugs ("NSAIDs") should alleviate the condition because NSAIDs inhibited prostaglandin synthetase ($PGE_2$) activity. Thus, he administered the nonsteroidal anti-inflammatory drug ("NSAID") sulindac (an inhibitor of $PGE_2$) to several FAP patients. Waddel discovered that polyps regressed and did not recur upon such therapy. $PGE_2$ inhibition results from the inhibition of cyclooxygenase (COX) caused by NSAIDs. The success by Waddell and the $PGE_2$/COX relationship seemingly confirmed the role of two other biochemical targets—$PGE_2$ and COX—in carcinogenesis, and the subsequent literature reinforced these views.

Sulindac and other NSAIDs when chronically administered, aggravate the digestive tract where $PGE_2$ plays a protective role. In addition, they exhibit side effects involving the kidney and interference with normal blood clotting. Thus for neoplasia patients, such drugs are not a practical chronic treatment for FAP. These side effects also prohibit NSAIDs' use for any other neoplasia indication requiring long-term drug administration.

Recent discoveries have lead scientists away from the COX/$PEG_2$ targets, since those targets do not appear to be the primary (or perhaps even secondary targets) to treat neoplasia patients successfully. Pamukcu et al., in U.S. Pat. No. 5,401,774, disclosed that sulfonyl compounds, that have been reported to be practically devoid of PGE2 and COX inhibition (and therefore not NSAIDs or anti-inflammatory compounds) unexpectedly inhibited the growth of a variety of neoplastic cells, including colon polyp cells. These sulfonyl derivatives have proven effective in rat models of colon carcinogenesis, and one variant (now referred to as exisulind) has proven effective in human clinical trials with FAP patients.

Thus like so many other proteins over-expressed in neoplasias, $PGE_2$/COX over-expression is not a cause of neoplasia, rather a consequence. But the discoveries by Pamucku et al., however, have raised the question about how their compounds act —what do such compounds do to neoplastic cells?

Piazza, et al. (in U.S. Pat. No. 5,858,694) discovered that compounds (such as the sulfonyl compounds above) inhibited cyclic GMP, phosphodiesterase, namely, PDE5 and that other such compounds could be screened using that enzyme, which could lead to the discovery of still other pharmaceutical compositions that are anti-neoplastic, and that can be practically devoid of COX or PGE2 inhibition. In addition, anti-neoplastic PDE5-inhibiting compounds can induce apoptosis (a form of programmed cell death or suicide) in neoplastic cells, but not in normal cells. Thus, the conventional wisdom that chemotherapeutics cannot be effective without also killing normal cells is being reversed by such discoveries.

Further, new research presented below has shown that not all compounds exhibiting PDE5 inhibitions induce apoptosis in neoplastic cells. For example, the well-known PDE5 inhibitors, zaprinast and sildenafil, do not induce apoptosis, or even inhibit cell growth in neoplastic cells in our hands, as explained below. However, because pro-apoptotic PDE5 inhibitors induced apoptosis selectively (i.e., in neoplastic but not in normal cells), and many did so without substantial COX inhibition, the usefulness of PDE5 as a screening tool for desirable anti-neoplastic compounds is unquestioned.

However, an even more accurate and selective screening tool than PDE5 to find anti-neoplastic, pro-apoptotic but safe compounds is desirable.

SUMMARY OF THE INVENTION

In the course of researching why some PDE5 inhibitors induced apoptosis while others did not, we uncovered a form of cyclic GMP-specific phosphodiesterase, not previously described. This new phosphodiesterase activity was previously uncharacterized, possibly because it is expressed only in neoplastic tissue, or perhaps because it is a mutation of a known/characterized PDE. This new PDE is useful in screening pharmaceutical compounds for desirable anti-neoplastic properties.

In its broadest aspects, this new PDE is characterized by having:
(a) cGMP specificity over cAMP
(b) positive cooperative kinetic behavior in the presence of cGMP substrate;
(c) submicromolar affinity for cGMP; and
(d) insensitivity to incubation with purified cGMP-dependent protein kinase Other characteristics of this novel PDE include: it has a reduced sensitivity to inhibition by zaprinast and E4021, it can be separated from classical PDE5 activity by anion-exchange chromatography, it is not activated by calcium/calmodulin, and it is insensitive to rolipram, vinpocetine and indolodan.

This invention relates to a novel in vitro method for screening test compounds for their ability to treat and prevent neoplasia, especially pre-cancerous lesions, safely. In particular, the present invention provides a method for identifying test compounds that can be used to treat and prevent neoplasia, including precancerous lesions. The compounds so identified can have minimal side effects attributable to COX inhibition and other non-specific interactions. The compounds of interest can be tested by exposing the novel PDE described above to the compounds, and if a compound inhibits this novel PDE, the compound is then further evaluated for its anti-neoplastic properties.

One aspect of this invention, therefore, involves a screening method to identify a compound effective for treating neoplasia that includes ascertaining the compound's inhibition of this novel PDE and its inhibition of COX. Preferably, the screening method of this invention further includes determining whether the compound inhibits the growth of tumor cells in a cell culture.

In another aspect, the screening method of this invention involves determining the COX inhibition activity of the compound, determining the inhibition activity of the compound against this novel PDE, and determining whether the compound induces apoptosis in tumor cells.

By screening compounds in this fashion, potentially beneficial and improved compounds for treating neoplasia can be identified more rapidly and with greater precision than possible in the past. Further benefits will be apparent from the detailed description that follows.

DETAILED DESCRIPTION OF THE PREFERRED EMBODIMENTS

I. The Novel cGMP-Specific Phosphodiesterase
A. Its Isolation

The isolated cGMP-specific phosphodiesterase was prepared from the human carcinoma cell line commonly referred to as SW480 available from the American Tissue Type Collection in Rockville, Md., U.S.A. SW480 is a human colon cancer cell line that originated from moderately differentiated epithelial adenocarcinoma.

Figure 1:
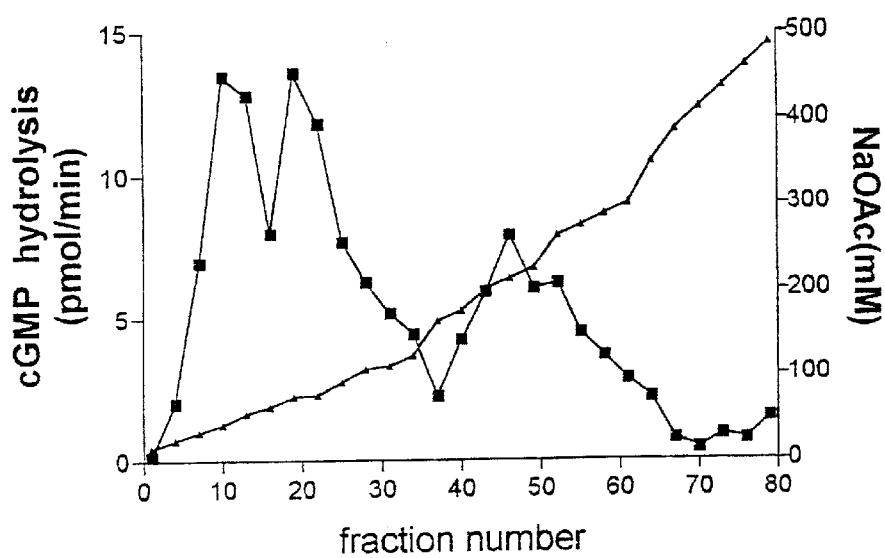
FIG. 1 is a graph of the cGMP activities of the cGMP phosphodiesterases obtained from SW480 neoplastic cells, as assayed from a the eluent from a DEAE-Trisacryl M column.

To isolate the novel phosphodiesterase, approximately four hundred million SW480 cells at confluence were scraped from 150 $cm^2$ tissue culture dishes after two washes with 10 ml cold PBS and pelleted by centrifugation. The cells were resuspended in homogenization buffer (20 ml TMPI-EDTA-Triton pH 7.4:20 mM Tris-HOAc, 5 mM $MgAc_2$, 0.1 mM EDTA, 0.8% Triton-100, 10 $\mu$M Benzamidine, 10 $\mu$M TLCK, 2000 U/mL Aprotinin, 2 $\mu$M Leupeptin, 2 $\mu$M Pepstatin A) and homogenized on an ice bath using a polytron tissumizer ( three times, 20 seconds/pulse). The homogenized material was centrifuged at 105,000 g for 60 minutes at 4° C. in a Beckman L8 ultracentrifuge, and the supernatant was diluted with TMPI-EDTA (60 ml) and applied to a 10-milliliter DEAE-Trisacryl M column pre-equilibrated with TMPI-EDTA buffer. The loaded column was washed with 60 mL of TM-EDTA, and PDE activities were eluted with a 120 ml linear gradient of NaOAc (0–0.5 M) in TM-EDTA, at a flow rate of 0.95 ml/minute, 1.4 ml/fraction. Eighty fractions were collected and assayed for cGMP hydrolysis immediately (i.e. within minutes). FIG. 1. shows the column's elution profile, revealing two initial peaks of cGMP PDE activity, A and B, which were eluted by 40–50 mM and 70–80 mM NaOAC. Respectively. As explained below, peak A is PDE5, whereas peak B is the novel phosphodiesterase of this invention.

Cyclic nucleotide PDE activity of each fraction was determined using the modified two-step radioisotopic method of Thompson et al. (Thompson W J, et al, Adv Cyclic Nucleotide Res 10: 69–92, 1979), as further described below. The reaction was in 400 $\mu$l containing Tris-HCl (40 mM; pH 8.0), $MgCl_2$ (5 mM), 2-mercaptoethanol (4 mM), bovine serum albumin (30 $\mu$g), cGMP (0.25 $\mu$M–5 $\mu$M) with constant tritiated substrate (200,000 cpm). The incubation time was adjusted to give less than 15% hydrolysis. The mixture was incubated at 30° C. followed by boiling for 45 seconds to stop the reaction. Then the mixture was cooled, snake venom (50 $\mu$g) added, and the mixture was incubated at 30° C. for 10 minutes. MeOH (1 ml) was added to stop the reaction, and the mixture was transferred to an anion-exchange column (Dowex 1-X8, 0.25 ml resin). The eluant was combined with a second ml of MeOH, applied to the resin, and after adding 6 ml scintillation fluid tritium activity was measured using a Beckman LS 6500 for one minute.

Figure 2:
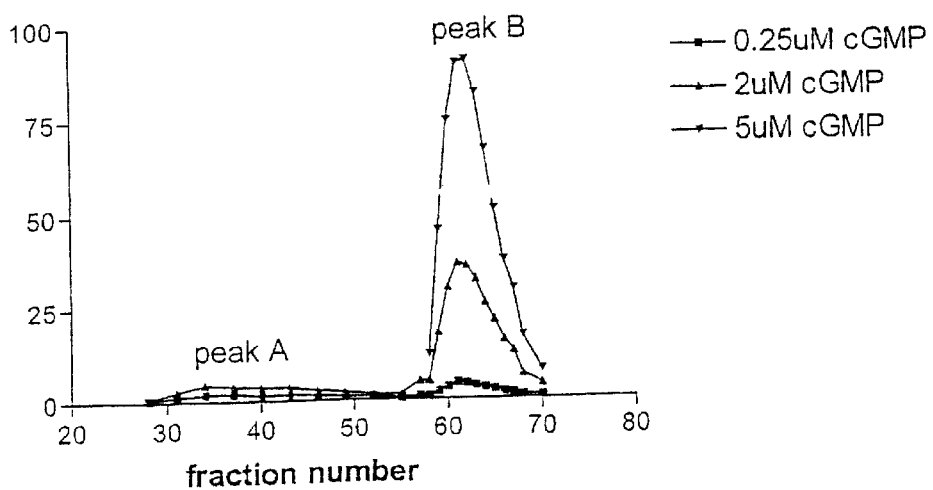
FIG. 2 is a graph of cGMP activities of the reloaded cGMP phosphodiesterases obtained from SW480 neoplastic cells, as assayed from a the eluent from a DEAE-Trisacryl M column.

To fractionate cGMP hydrolytic activity of peaks A and B further, fractions 15 to 30 of the original 80 were reloaded onto the DEAE-Trisacryl M column and eluted with a linear gradient of NaOAc (0–0.5 M) in TM-EDTA. Fractions were again immediately assayed for cGMP hydrolysis (using the procedure described above with 0.2, 2, 5 $\mu$M substrate), the results of which are graphically presented in FIG. 2. One novel observation about peak B illustrated in FIG. 2 is that increasing substrate concentration of cGMP dramatically enhanced activity when contrasted to peak A. Peak A activity shows apparent substrate saturation of high affinity catalytic sites.

B. cGMP-Specifilty of PDE Peaks A and B

Each fraction from the DEAE column was also assayed for cGMP-hydrolysis activity (0.25 $\mu$M cGMP) in the presence or absence of $Ca^{++}$, or $Ca^{++}$-CaM and/or EGTA and for cAMP (0.25 $\mu$M cAMP) hydrolysis activity in the presence or absence of 5 $\mu$M cGMP. Neither PDE peak A and peak B (fractions 5–22; see FIG. 1) hydrolyzed cAMP significantly, establishing that neither was a cAMP hydrolysing gene family of PDE (i.e. a PDE 1, 2, 3).

Ca++ (with or without calmodulin) failed to activate either cAMP or cGMP hydrolysis activity of either peak A or B, and cGMP failed to activate or inhibit cAMP hydrolysis. Such results establish that peaks A and B constitute cGMP-specific PDEs but not PDE1, PDE2, PDE3 or PDE4.

For PDE peak B, as discussed below, cyclic GMP activated the cGMP hydrolytic activity of the enzyme, but did not activate any cAMP hydrolytic activity. This reveals that PDE peak B—the novel phosphodiesterase of this invention—is not a cGMP-stimulated cAMP hydrolysis ("cGS") or among the PDE2 family isoforns because the known isoforms of PDE2 hydrolyze both cGMP and cAMP.

C. Peak A Is A PDE5, But Peak B—A New cGMP-Specific PDE—Is Not

To characterize any PDE isoform, kinetic behavior and substrate preference should be assessed.

Peak A showed typical "PDE5" characteristics. For example, the $K_m$ of the enzyme for cGMP was 1.07 $\mu$M, and Vmax was 0.16 nmol/min/mg. In addition, as discussed below, zaprinast ($IC_{50}$=1.37 $\mu$M) and E4021 ($IC_{50}$=3 nM) and sildenafil inhibited activity of peak A. Further, zaprinast showed inhibition for cGMP hydrolysis activity of peak A, consistent with results reported in the literature.

Figure 3:
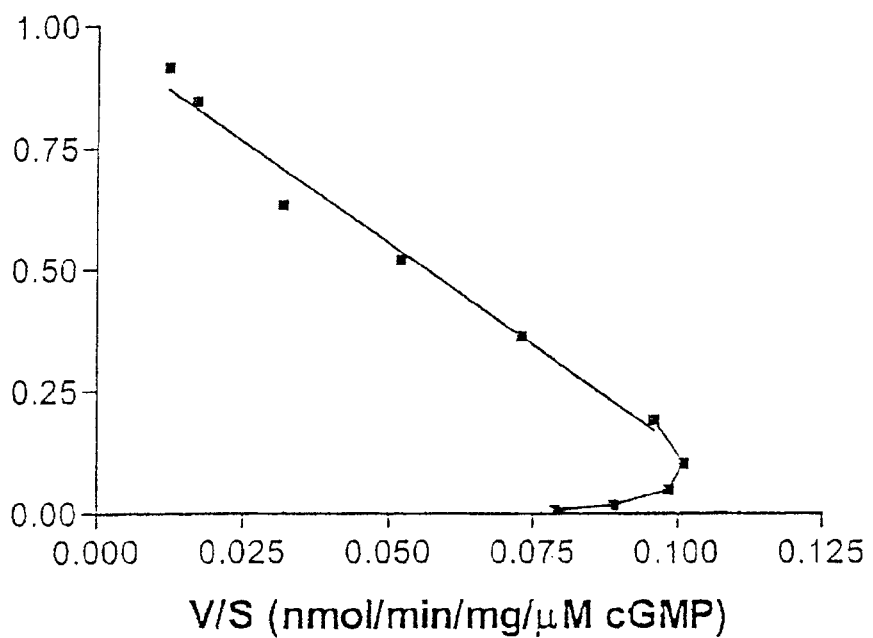
FIG. 3 is a graph of the kinetic behavior of the novel PDE of this invention.

PDE Peak B showed considerably different kinetic properties as compared to PDE peak A. For example, in Eadie-Hofstee plots of Peak A, cyclic GMP hydrolysis shows single line with negative slope with increasing substrate concentrations, indicative of Michaelis-Menten kinetic behavior. Peak B, however, shows the novel property for cGMP hydrolysis in the absence of cAMP of a decreasing (apparent $K_m$=8.4), then increasing slope ($K_m$<1) of Eadie-Hotfstee plots with increasing cGMP substrate (see, FIG. 3). Thus, this establishes Peak B's submicromolar affinity for cGMP (i.e., where $K_m$<1).

Consistent with the kinetic studies (i.e. FIG. 3) and postive-cooperative kinetic behavior in the presence of cGMP substrate, was the increased cGMP hydrolytic activity in the presence of increasing concentrations of cGMP substrate. This was discovered by comparing 0.25 $\mu$M, 2 $\mu$M and 5 $\mu$M concentrations of cGMP in the presence of PDE peak B after a second DEAE separation to rule out cAMP hydrolysis and to rule out this new enzyme being a "classic" PDE5. Higher cGMP concentrations evoked disproportionately greater cGMP hydrolysis with PDE peak B, as shown in FIG. 2.

These observations suggest that cGMP binding to the peak B enzyme causes a conformational change in the enzyme.

D. Zaprinast- and Sildenafil-Insensitivity of PDE Peak B Relative to Peak A, and Their Effects on Other PDE Inhibitors Different PDE inhibitors were studied using twelve concentrations of drug from 0.01 to 100 $\mu$M and substrate concentration of 0.25 $\mu$M $^3$H-cGMP. $IC_{50}$ values were calculated with variable slope, sigmoidal curve fits using Prism 2.01 (GraphPad). The results are shown in Table 1. While compounds E4021 and zaprinast inhibited peak A, (with high affinities) $IC_{50}$ values calculated against peak B are significantly increased (>50 fold). This confirms that peak A is a PDE5. These data further illllustrate that the novel PDE of this invention is, for all practical purposes, zaprinast-insensitive and E4021-insensitive.

TABLE 1

Comparison of PDE Inhibitors Against Peak A and Peak B (cGMP Hydrolysis)

| Compound | PDE Family Inhibitor | $IC_{50}$ Peak A ($\mu$M) | $IC_{50}$ Peak B ($\mu$M) | Ratio ($IC_{50}$ Peak A/ Peak B) |
|---|---|---|---|---|
| E4021 | 5 | 0.003 | 8.4 | 0.0004 |
| Zaprinast | 5 | 1.4 | >30 | <0.05 |
| Compound E | 5 and others | 0.38 | 0.37 | 1.0 |
| Sulindac sulfide | 5 and others | 50 | 50 | 1.0 |
| Vinpocetine | 1 | >100 | >100 | |
| EHNA | 2,5 | >100 | 3.7 | |
| Indolidan | 3 | 31 | >100 | <0.31 |
| Rolipram | 4 | >100 | >100 | |
| Sildenafil | 5 | .0003 | >10 | <.00003 |

By contrast, sulindac sulfide and Compound E and competitively inhibited both peaks A and B phosphodiesterases at the same potency ($IC_{50}$=0.38 $\mu$M for PDE peak A; 0.37 $\mu$M for PDE peak B).

There is significance for the treatment of neoplasia and the screening of useful compounds for such treatment in the fact that peak B is zaprinast-insensitive whereas peaks A and B are both sensitive to sulindac sulfide and Compound E. We have tested zaprinast, E4021 and sildenafil to ascertain whether they induce apoptosis or inhibit the growth of neoplastic cells, and have done the same for Compound E. As explained below, zaprinast does not have significant apoptosis-inducing or growth-inhibiting properties, whereas sulindac sulfide and Compound E are precisely the opposite. In other words, the ability of a compound to inhibit both PDE peaks A and B correlates with its ability to induce apoptosis in neoplastic cells, whereas if a compound (e.g., zaprinast) has specifity for PDE peak A only, that compound will not induce apoptosis.

E. Insensitivity of PDE Peak B To Incubation With cGMP-Dependent Protein Kinase G Further differences between PDE peaks A and B were observed in their respective cGMP-hydrolytic activities in the presence of varying concentrations of cGMP-dependent protein kinase G (which phosphorylates typical PDE5). Specifically, peak A and peak B fractions were incubated with different concentrations of protein kinase G at 30° C. for 30 minutes. Cyclic GMP hydrolysis of both peaks has assayed after phosphorylation was attempted. Consistent with previously published information about PDE5, Peak A showed increasing cGMP hydrolysis activity in response to protein kinase G incubation, indicating that Peak A was phosphorlyated. Peak B was unchanged, however (i.e. was not phosphorylated and insensitive to incubation with cGMP-dependent protein kinase G). These data are consistent with Peak A being a PDE5 family isoform and Peak B being a novel cGMP PDE.

II. Screening Pharmaceutical Compositions Using The New PDE

A. In General

The novel PDE of this invention is useful to identify compounds that can be used to treat or prevent neoplasms, and that are not characterized by serious side effects.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a test compound is important to the discovery of a relevant target for pharmaceutical therapy. Screening assays based on this technology can be combined with other tests to determine which compounds have growth inhibiting and pro-apoptotic activity.

This invention is the product of several important discoveries. First, the present inventors discovered that desirable inhibitors of tumor cell growth induce premature death of cancer cells by apoptosis (see, Piazza, G. A., et al., *Cancer Research*, 55(14), 3110–16, 1995). Second, the present inventors unexpectedly discovered compounds that selectively induce apoptosis without substantial COX inhibition also inhibit PDE5. In particular, and contrary to leading scientific studies, desirable compounds for treating neoplastic lesions inhibit PDE5 (EC 3.1.4.17). PDE5 is one of at least ten gene families of phosphodiesterase. PDE5 and the novel PDE of this invention are unique in that they selectively degrade cyclic GMP and not cAMP, while the other famlies of PDE selectively degrade/hydrolyze cAMP and not cGMP or non-selectively degrade both cGMP and cAMP. Preferably, desirable compounds used to treat neoplasia do not substantially inhibit non-selective or cAMP degrading phosphodiesterase types.

B. COX Screening

A preferred embodiment of the present invention involves determining the cyclooxygenase inhibition activity of a given compound, and determining the cGMP specific PDE inhibitory activity of the compound. The test compounds are scored for their probable ability to treat neoplastic lesions either directly or indirectly by comparing their activities against known compounds useful for treating neoplastic lesions. A standard compound that is known to be effective for treating neoplastic lesions without causing gastric irritation is 5-fluoro-2-methyl-1-(p-methylsulfonylbenzylidene)-3-indenylacetic acid ("exisulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit (cGMP-specific PDEs, such as 1-(3-chloroanilino)-4-phenyphthalazine ("MY5445").

As used herein, the term "precancerous lesion" includes syndromes represented by abnormal neoplastic, including dysplastic, changes of tissue. Examples include dysplastic growths in colonic, breast, prostate or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, lung, prostatic dysplasia, prostatic intraneoplasia, breast and/or skin and related conditions (e.g., actinic keraosis), whether the lesions are clinically identifiable or not.

As used herein, the terms "carcinoma" or "cancer" refers to lesions which are cancerous. Examples include malignant melanomas, breast cancer, prostate cancer and colon cancer. As used herein, the terms "neoplasia" and "neoplasms" refer to both cancerous and pre-cancerous lesions.

As used herein, the abbreviation PG represents prostaglandin; PS represents prostaglandin synthetase; $PGE_2$ represents prostaglandin $E_2$; PDE represents phosphodiesterase; COX represents cyclooxygenase; cyclic nucleotide, RIA represents - radioimmunoassay.

COX inhibition by a test compound can be determined by either of two methods. One method involves measuring $PGE_2$ secretion by intact HL-60 cells following exposure to the compound being screened. The other method involves measuring the activity of purified cyclooxygenases (COXs) in the presence of the compound. Both methods involve protocols previously described in the literature, but preferred protocols are set forth below.

Compounds of can be evaluated to determine whether they inhibit the production of prostaglandin $E_2$ ("$PGE_2$"), by measuring $PGE_2$. Using an enzyme immunoassay (EIA) kit for $PGE_2$, such as commercially available from Amersham, Arlington Heights, Ill. U.S.A. Suitable cells include those that make an abundance of PG, such as HL-60 cells. HL-60 cells are human promyelocytes that are differentiated with DMSO into mature granulocytes (See, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.*, 149:969–974, 1979). These differentiated cells produce $PGE_2$ after stimulation with a calcium ionophore, A23187 (see, Kargman, S., Prasit, P. and Evans, J. F., "Translocation of HL-60 Cell 5-Lipoxygenase",*J. Biol. Chem.*, 266: 23745–23752, 1991). HL-60 are available from the American Type Culture Collection (ATCC:CCL240). They can be grown in a RPMI 1640 medium supplemented with 20% heat-inactivated fetal bovine serum, 50 $\mu$U/ml penicillin and 50 $\mu$g/ml streptomycin in an atmosphere of 5% $CO_2$ at 37° C. To induce myeloid differentiation, cells are exposed to 1.3% DMSO for 9 days and then washed and resuspended in Dulbecco's phosphate-buffered saline at a concentration of $3 \times 10^6$ cells/ml.

The differentiated HL-60 cells ($3 \times 10^6$ cells/ml) are incubated for 15 minutes at 37° C. in the presence of the compounds tested at the desired concentration. Cells are then stimulated by A23187 ($5 \times 10^{-6}$ M) for 15 minutes. $PGE_2$ secreted into the external medium is measured as described above.

As indicated above, a second method to assess COX inhibition of a test compound is to measure the COX activity in the presence of a test compound. Two different forms of cyclooxygenase (COX-I and COX-2) have been reported in the literature to regulate prostaglandin synthesis. COX-2 represents the inducible form of COX while COX-I represents a constitutive form. COX-I activity can be measured using the method described by Mitchell et al. ("Selectivity of Nonsteroidal Anti-inflammatory Drugs as Inhibitors of Constitutive and Inducible Cyclooxygenase," *Proc. Natl. Acad. Sci. USA.*, 90:11693–11697, 1993, which is incorporated herein by reference) using COX-I purified from ram seminal vesicles as described by Boopathy & Balasubramanian, "Purification And Characterization Of Sheep Platelet Cyclooxygenase" (*Biochem. J.*, 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 minutes with 100 $\mu$M arachidonic acid (Sigma Chemical Co.), cofactors (such as 1.0 mM glutathione, 1.0 mM hydroquinone, 0.625 $\mu$M hemoglobin and 1.25 mM $CaCl_2$ in 100 mM Tris-HCl, pH 7.4) and the drug to be tested. Following incubation, the reaction can be terminated with trichloroacetic acid. After stopping the reaction by adding thiobarbituric acid and malonaldehyde, enzymatic activity can then be measured spectrophotometrically at 530 nm.

Obviously, a compound that exhibits minimal COX-I or COX-2 inhibitory activity in relation to its greater PDE5/ novel PDE inhibitory activity may be a desirable test compound.

The amount of COX inhibition is determined by comparing the activity of the cyclooxygenase in the presence and absence of the test compound. Residual (i.e., less than about 25%) or no COX inhibitory activity at a concentration of about 100 $\mu$M is indicative that the compound should be evaluated further for usefulness for treating neoplasia. Preferably, the $IC_{50}$ should be greater than 1000 $\mu$M for the compound to be further considered potential use.

C. Determining Phosphodiesterase Inhibition Activity

Compounds can be screened for inhibitory effect on the activity of the novel phosphodiesterase of this invention using either the enzyme isolated as described above, a recombinant version, or using the novel PDE together with PDE5. Alternatively, cyclic nucleotide levels in whole cells are measured by RIA and compared to untreated and zaprinast-treated cells.

Phosphodiesterase activity can be determined using methods known in the art, such as a method using radioactive $^3$H cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 $\mu$M; 100,000 cpm; containing 40 mM Tris-HCl (pH 8.0), 5 mM $MgCl_2$ and 1 mg/ml BSA) is mixed with the drug to be tested in a total volume of 400 $\mu$l. The mixture is incubated at 30° C. for 10 minutes with isolated PDE of this invention. Reactions are terminated, for example, by boiling the reaction mixture for 75 seconds. After cooling on ice, 100 $\mu$l of 0.5 mg/ml snake venom (O. Hannah venom available from Sigma) is added and incubated for 10 minutes at 30° C. This reaction is then terminated by the addition of an alcohol, e.g. 1 ml of 100% methanol. Assay samples are applied to 1 ml Dowex 1-X8 column; and washed with 1 ml of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterase of this invention is reflected by an increase in cGMP in neoplastic cells exposed to a compound being screened. The amount of PDE activity can be determined by assaying for the amount of cyclic GMP in the extract of treated cells using radioimmunoassay (RIA). In this procedure, HT-29 or SW-480 cells are plated and grown to confluency. As indicated above, SW-480 contains both PDE5 and the novel PDE of this invention, so when PDE activity is evaluated in this fashion, a combined cGMP hydrolytic activity is assayed simultaneously. The test compound is then incubated with the cell culture at a concentration of compound between about 200 $\mu$M to about 200 $\mu$M. About 24 to 48 hours thereafter, the culture media is removed from the cells, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). Iodinated ligands (tyrosine metheyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition, the culture media may be acidified, frozen (−70° C.) and also analyzed for cGMP and cAMP.

In addition to observing increases in the content of cGMP in neoplastic cells caused by desirable test compounds, decreases in content of cAMP have also been observed. It has been observed that a particularly desirable compound (i.e. one that selectively induces apoptosis in neoplastic cells, but not substantially in normal cells) follows a time course consistent with cGMP-specific PDE inhibition as one initial action resulting in an increased cGMP content within minutes. Secondarily, treatment of neoplastic cells with a desirable anti-neoplastic compound leads to decreased cAMP content within 24 hours. The intracellular targets of drug actions are being studied further, but current data support the concept that the initial rise in cGMP content and the subsequent fall in cAMP content precede apoptosis in neoplastic cells exposed to desirable compounds.

The change in the ratio of the two cyclic nucleotides may be a more accurate tool for evaluating desirable cGMP-specific phosphodiesterase inhibition activity of test compounds, rather than measuring only the absolute value of cGMP, only cGMP-specific phosphodiesterase inhibition, or only the level of cGMP hydrolysis. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure intact cell cAMP, $^3$H-adenine prelabeling is used according to published procedures (Whalin M. E., R. L. Garrett Jr., W. J. Thompson, and S. J. Strada, "Correlation of cell-free brain cyclic nucleotide phosphodiesterase activities to cyclic AMP decay in intact brain slices", *Sec. Mess. and Phos. Protein Research*, 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell prelabeling according to published procedures (Reynolds, P. E., S. J. Strada and W. J. Thompson, "Cyclic GMP accumulation in pulmonary microvascular endothelial cells measured by intact cell prelabeling," *Life Sci.*, 60:909–918, 1997, which is incorporated herein by reference).

The PDE inhibitory activity effect of a test compound can also be determined from a tissue sample. Tissue biopsies from humans or tissues from anestesized animals arc collected from subjects exposed to the test compound. Briefly, a sample of tissue is homogcnized in 500 $\mu$l of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 $\mu$l of assay buffer. The amount of cGMP-specific inhibition is determnined by assaying for the amount of cyclic nucleotides using RIA procedures as described above.

The amount of inhibition is determined by comparing the activity of the novel PDE in the presence and absence of the test compound. Inhibition of the novel PDE activity is indicative that the compound is useful for treating neoplasia. Significant inhibitory activity greater than that of the benchmark, exisulind, preferably greater than 50% at a concentration of 10 $\mu$M or below, is indicative that a compound should be further evaluated for antineoplastic properties. Preferably, the IC$_{50}$ value for the novel PDE inhibition should be less than 50 $\mu$M for the compound to be further considered for potential use.

D. Determining Whether A Compound Reduces The Number Of Tumor Cells

In an alternate embodiment, the screening method of the present invention involves further determining whether the compound reduces the growth of tumor cells. Various cell lines can be used in the sample depending on the tissue to be tested. For example, these cell lines include: SW-480 - colonic adenocarcinoma; HT-29—colonic adenocarcinoma, A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

A compound's ability to inhibit tumor cell growth can be measured using the HT-29 human colon carcinoma cell line obtained from ATCC (Bethesda, MD). HT-29 cells have previously been characterized as a relevant colon tumor cell culture model (Fogh, J., and Trempe, G. *In: Human Tumor Cells in Vitro,* J. Fogh (eds.), Plenum Press, N.Y., pp. 115–159, 1975). HT-29 cells are maintained in RPMI media supplemented with 5% fetal bovine calf serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of test compound. Each determination of cell number involved six replicates. After six days in culture, the cells are fixed by the addition of cold trichloroacetic acid to a final concentration of 10% and protein levels are measured using the sulforhodamine B (SRB) colorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 50% at a dose of 100 $\mu$M or below is further indicative that the compound is useful for treating neoplastic lesions. Preferably, an IC$_{50}$ value is determined and used for comparative purposes. This value is the concentration of drug needed to inhibit tumor cell growth by 50% relative to the control. Preferably, the IC$_{50}$ value should be less than 100 $\mu$M for the compound to be considered further for potential use for treating neoplastic lesions.

E. Determining Whether A Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., *Cancer Research*, 55:3110–16, 1995, which is incorporated herein by reference). The novel features include collecting both floating and attached cells, identification of the optimal treatment times and dose range for observing apoptosis, and identification of optimal cell culture conditions.

Following treatment with a test compound, cultures can be assayed for apoptosis and necrosis by florescent microscopy following labeling with acridine orange and ethidium bromide. The method for measuring apoptotic cell number has previously been described by Duke & Cohen, "Morphological And Biochemical Assays Of Apoptosis," *Current Protocols In Immunology*, Coligan et al., cds., 3.17.1–3.17.16 (1992, which is incorporated herein by reference).

For example, floating and attached cells can be collected by trypsinization and washed three times in PBS. Aliquots of cells can be centrifuged. The pellet can then be resuspended in media and a dye mixture containing acridine orange and ethidium bromide prepared in PBS and mixed gently. The mixture can then be placed on a microscope slide and examined for morphological features of apoptosis.

Apoptosis can also be quantified by measuring an increase in DNA fragmentation in cells which have been treated with test compounds. Commercial photometric EIA for the quantitative in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged and the supernatant is removed. The cell pellet in each well is then resuspended in lysis buffer for 30 minutes. The lysates are then centrifuged and aliquots of the supernatant (i.e. cytoplasmic fraction) are transferred into a streptavidin-coated MTP. Care is taken not to shake the lysed pellets (i.e. cell nucleii containing high molecular weight, unfragmented DNA) in the MTP. Samples are then analyzed.

Fold stimulation (FS=$OD_{max}/OD_{veh}$), an indicator of apoptotic response, is determined for each compound tested at a given concentration. $EC_{50}$ values may also be determined by evaluating a series of concentrations of the test compound.

Statistically significant increases of apoptosis (i.e., greater than 2 fold stimulation at a concentration of 100 $\mu$M) are further indicative that the compound is useful for treating neoplastic lesions. Preferably, the $EC_{50}$ value for apoptotic activity should be less than 100 $\mu$M for the compound to be further considered for potential use for treating neoplastic lesions. $EC_{50}$ is herein defined as the concentration that causes 50% induction of apoptosis relative to vehicle treatment.

F. Mammary Gland Organ Culture Model Tests

Test compounds identified by the above methods can be tested for antineoplastic activity by their ability to inhibit the incidence of preneoplastic lesions in a mammary gland organ culture system. This mouse mammary gland organ culture technique has been successfully used by other investigators to study the effects of known antineoplastic agents such as NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed and thoracic mammary glands are excised aseptically and incubated for ten days in growth media supplemented with insulin, prolactin, hydrocortisone, and aldosterone. DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the premalignant lesions.

The test compound is dissolved in DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the unregressed structures is also outlined on the digitization pad and quantitated by the computer.

EXPERIMENTAL RESULTS

A number of compounds were examined in the various protocols and screened for potential use in treating neoplasia. The results of these tests are reported below. The test compounds are hereinafter designated by a letter code that corresponds to the following:

A—rac-threo-(E)-1-(N,N'-diethylaminoethanethio)-1-(butan-1',4'-olido)-[3', 4':1,2]-6-fluoro-2-methyl-3-(p-methylsulfonylbenzylidene)-indan;

B—(Z)-5-Fluoro-2-methyl-1-(3 ,4,5-trimethoxybenzylidene)-3-acetic acid;

C—(Z)-5-Fluoro-2-methyl-1-(p-chlorobenzylidene)-3-acetic acid;

D—rac-(E)-1-(butan-1',4'-olido)-[3',4':1,2]-6-fluoro-2-methyl-3-(p-methylsul fonylbenzylidene)-1S-indanyl-N-acetylcysteine;

E—(Z)-5-Fluoro-2-methyl-1-(3,4,5-trimethoxybenzylidcne)-3-indenylacetamide, N-benzyl;

F—(Z)-5-Fluoro-2-methyl-1-(p-methylsulfonylbenzylidene)-3-indenylacetamide, N,N'-dicyclohexyl;

G ribo-(E)-1-Triazolo-[2',3': 1",3"]-1-(butan-1,4'-olido)-[3',4':1,2]-6-fluoro-2-methyl-3-(p-methylsulfonylbenzylidene)-indan; and H—rac-(E)-1-(butan-1',4'-olido)-[3',4':1,2]-6-fluoro-2-methyl-3-(p-methylsulfonylbenzylidene)-1S-indanyl-glutathione).

EXAMPLE 1

COX Inhibition Assay

Figure 4:
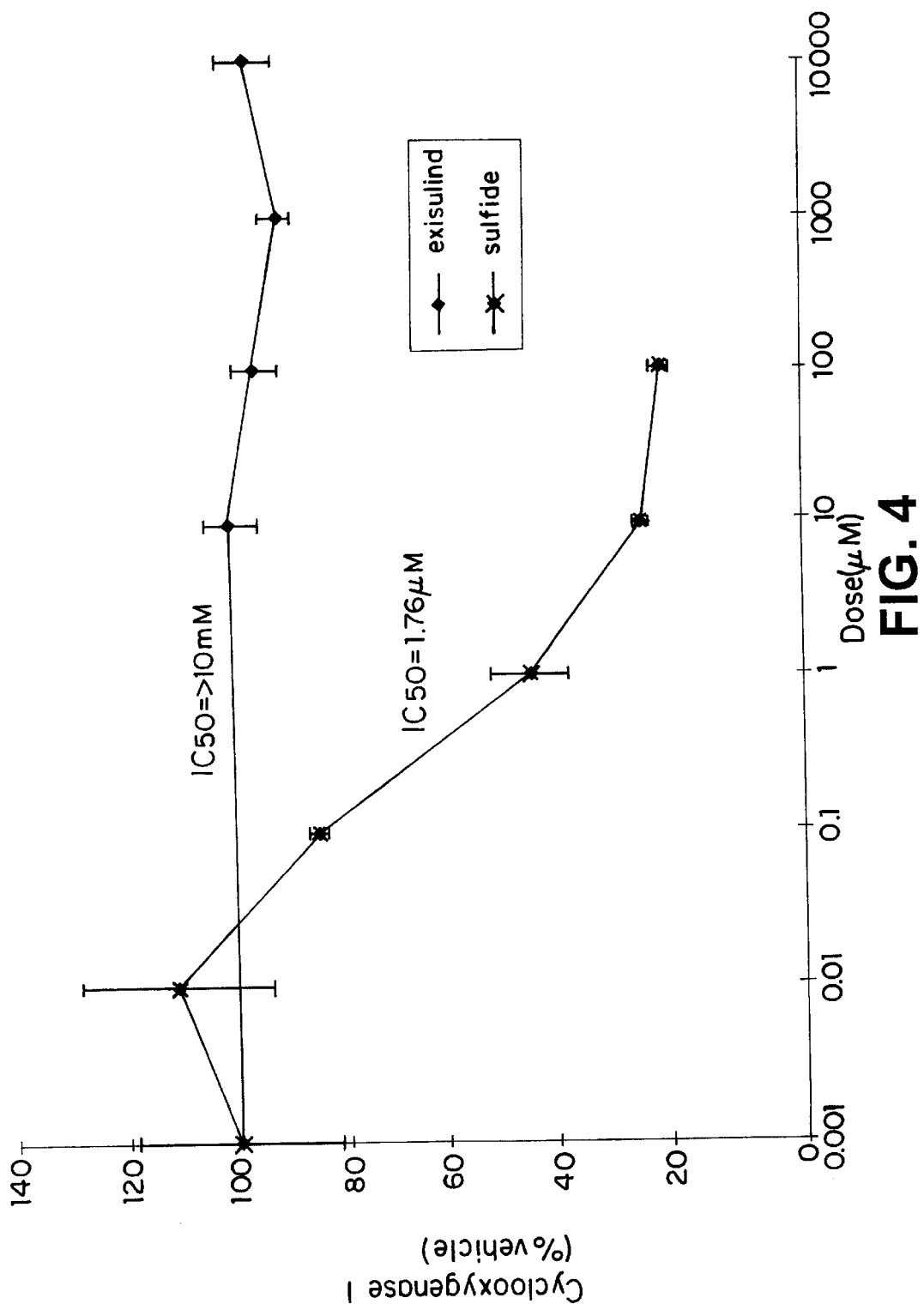
FIG. 4 illustrates the effect of the sulfide derivative of sulindac and the sulfone derivative of sulindac (a.k.a. exisulind) on purified cyclooxygenase activity.

Reference compounds and test compounds were analyzed for their COX inhibitory activity in accordance with the protocol for the COX assay, supra. FIG. 4 shows the effect of various concentrations of either sulindac sulfide or exisulind on purified cyclooxygenase (Type 1) activity. Cyclooxygenase activity was determined using purified cyclooxygenase from ram seminal vesicles as described previously (Mitchell et al, supra). The $IC_{50}$ value for sulindac sulfide was calculated to be approximately 1.76 $\mu$M, while that for exisulind was greater than 10,000 $\mu$M. These data show that sulindac sulfide, but not exisulind, is a COX-I inhibitor. Similar data were obtained for the COX-2 isoenzyme (Thompson, et al., Journal of the National Cancer Institute, 87: 1259–1260, 1995).

Figure 5:
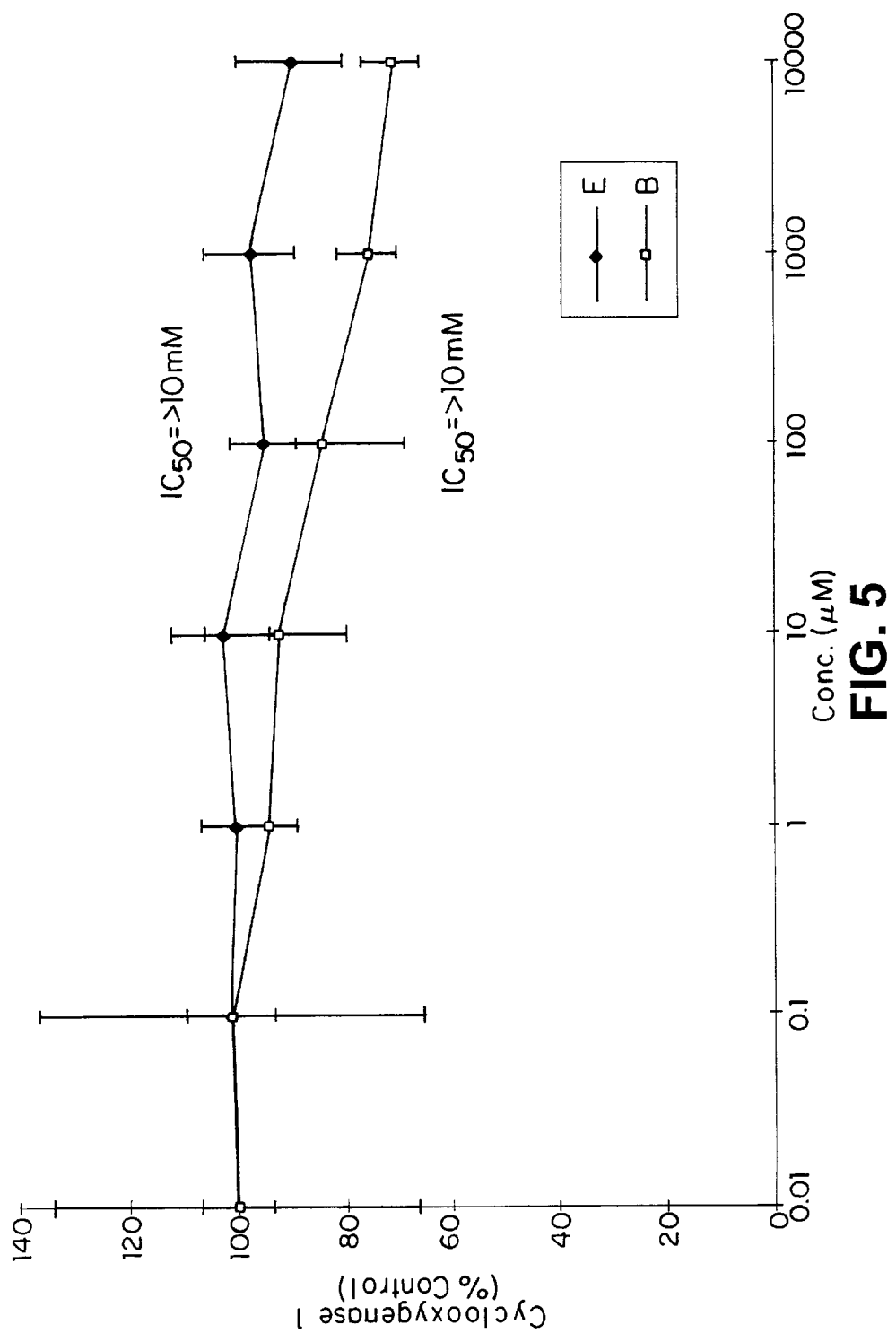
FIG. 5 illustrates the effects of test compounds B and E on COX inhibition.

FIG. 5 shows the effect of test compounds B and E on COX inhibition. COX activity was determined as for the compounds shown in FIG. 4. The data show that neither test compound B and E significantly inhibit COX-I.

TABLE 2

Cyclooxygenase inhibitory activity among a series of compounds

|  | % Inhibition at 100 $\mu$M |
|---|---|
| Reference compounds |  |
| Indomethacin | 95 |
| MY5445 | 94 |
| Sulindac sulfide | 97 |
| Exisulind | <25 |
| Test compounds |  |
| A | <25 |
| B | <25 |
| C | 87 |
| D | <25 |
| E | <25 |

In accordance with the protocol, spra, compounds A through E were evaluated for COX inhibitory activity as reported in Table 2 above. Compound C was found to inhibit COX greater than 25% at a 100 $\mu$M dose, and therefore, would not be selected for further screening.

EXAMPLE 2 cGMP PDE inhibition assay

Figure 6:
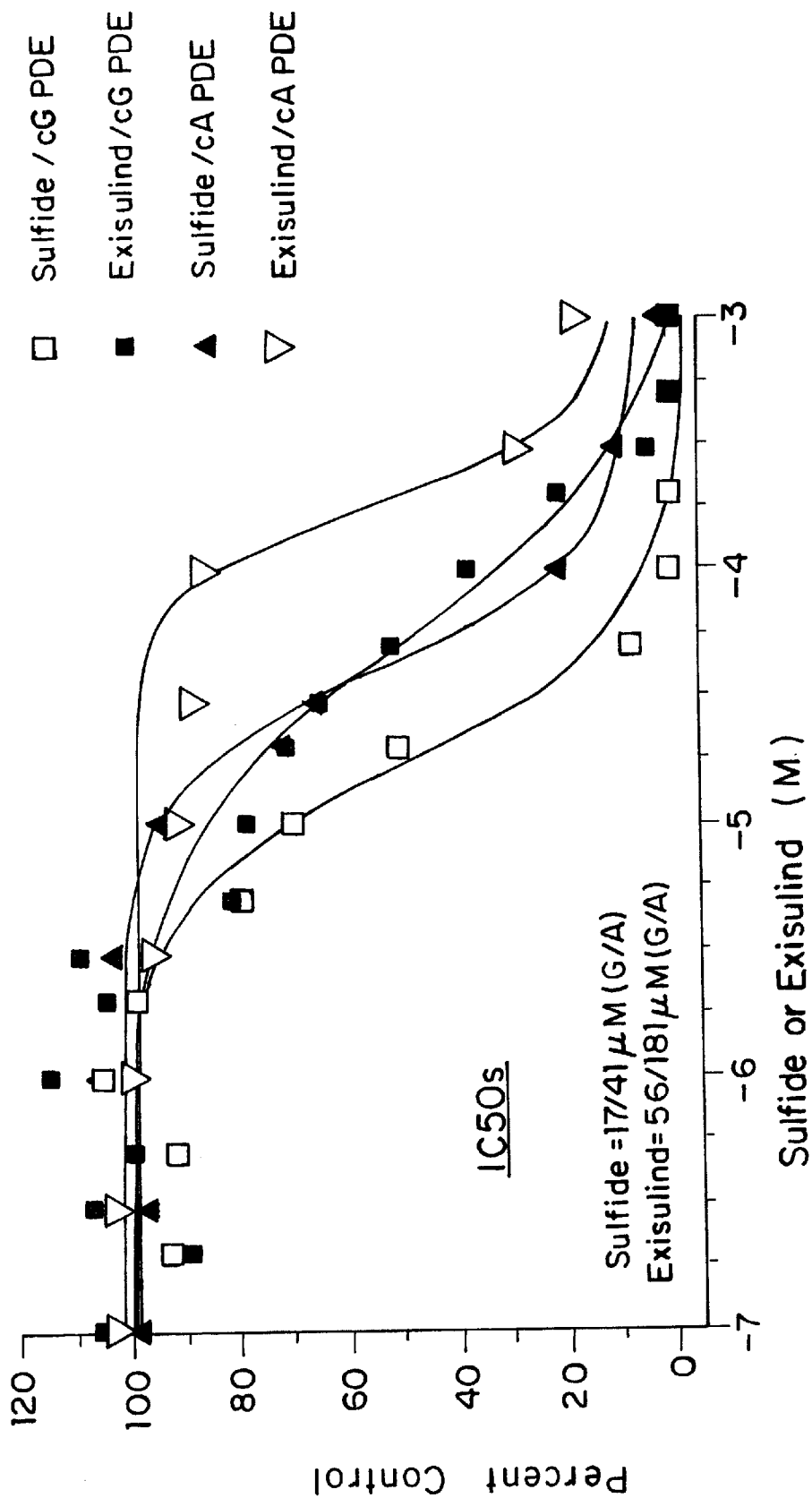
FIG. 6 illustrates the inhibitory effects of sulindac sulfide and exisulind on PDE4 and PDE5 purified from cultured tumor cells.

Reference compounds and test compounds were analyzed for their cGMP PDE inhibitory activity in accordance with the protocol for the assay described supra. FIG. 6 shows the effect of various concentrations of sulindac sulfide and exisulind on either PDE4 or cGMP PDE activity purified from human colon HT-29 cultured tumor cells, as described previously (W. J. Thompson et al., supra). The $IC_{50}$ value of sulindac sulfide for inhibition of PDE4 was 41 $\mu$M, and for inhibition of cGMP PDE was 17 $\mu$M. The $IC_{50}$ value of exisulind for inhibition of PDE4 was 181 $\mu$M, and for inhibition of cGMP PDE was 56 $\mu$M. These data show that both sulindac sulfide and exisulind inhibit phosphodiesterase activity. Both compounds show selectivity for the cGMP PDE isoenzyme forms over PDE4 isoforms.

Figure 7A:
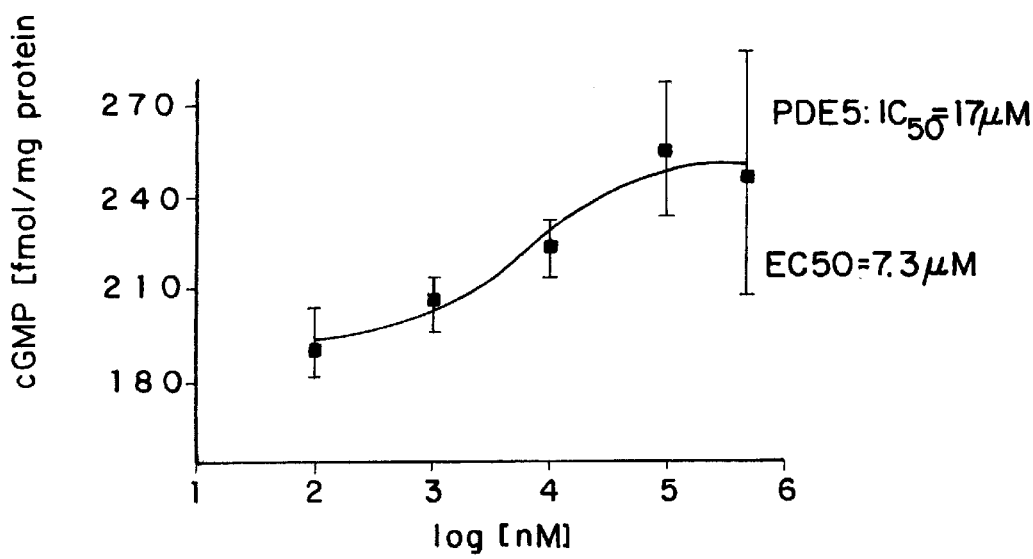
FIG. 7A illustrates the effects of sulindac sulfide on cGMP levels in HT29 cells.
Figure 7B:
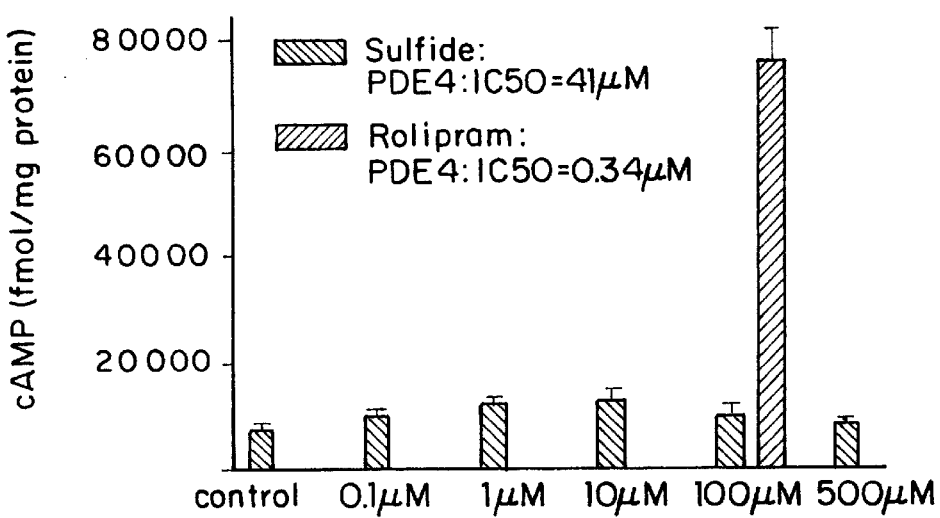
FIG. 7B illustraes the effects of sulindac sulfide on cAMP levels in HT29 cells.

FIG. 7 shows the effects of sulindac sulfide on either cGMP or cAMP production as determined in cultured HT-29 cells in accordance with the assay described, supra. HT-29 cells were treated with sulindac sulfide for 30 minutes and cGMP or cAMP was measured by conventional radioimmunoassay method. As indicated, sulindac sulfide increased the levels of cGMP by greater than 50% with an $EC_{50}$ value of 7.3 $\mu$M (7A top). Levels of cAMP were unaffected by treatment, although a known PDE4 inhibitor, rolipram, increased cAMP (7B bottom). The data demonstrate the pharmacological significance of inhibiting cGMP PDE, relative to PDE4.

Figure 8:
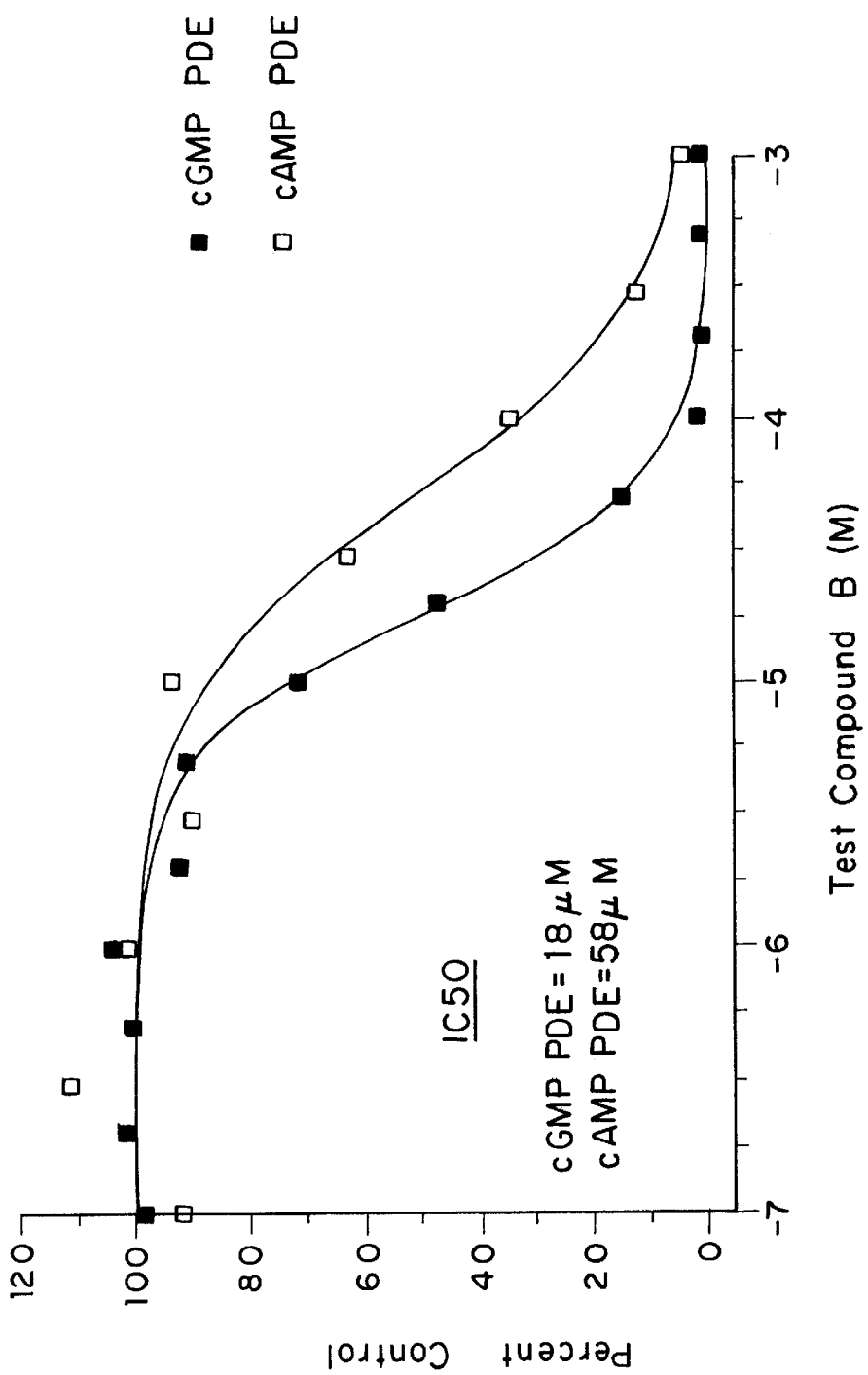
FIG. 8 illustrates the phosphodiesterase inhibitory activity of compound B.

FIG. 8 shows the effect of the indicated dose of test compound B on either cGMP PDE or PDE4 isozymes of phosphodiesterase. The calculated $IC_{50}$ value was 18 $\mu$M for cGMP PDE and was 58 $\mu$M for PDE4.

Figure 9:
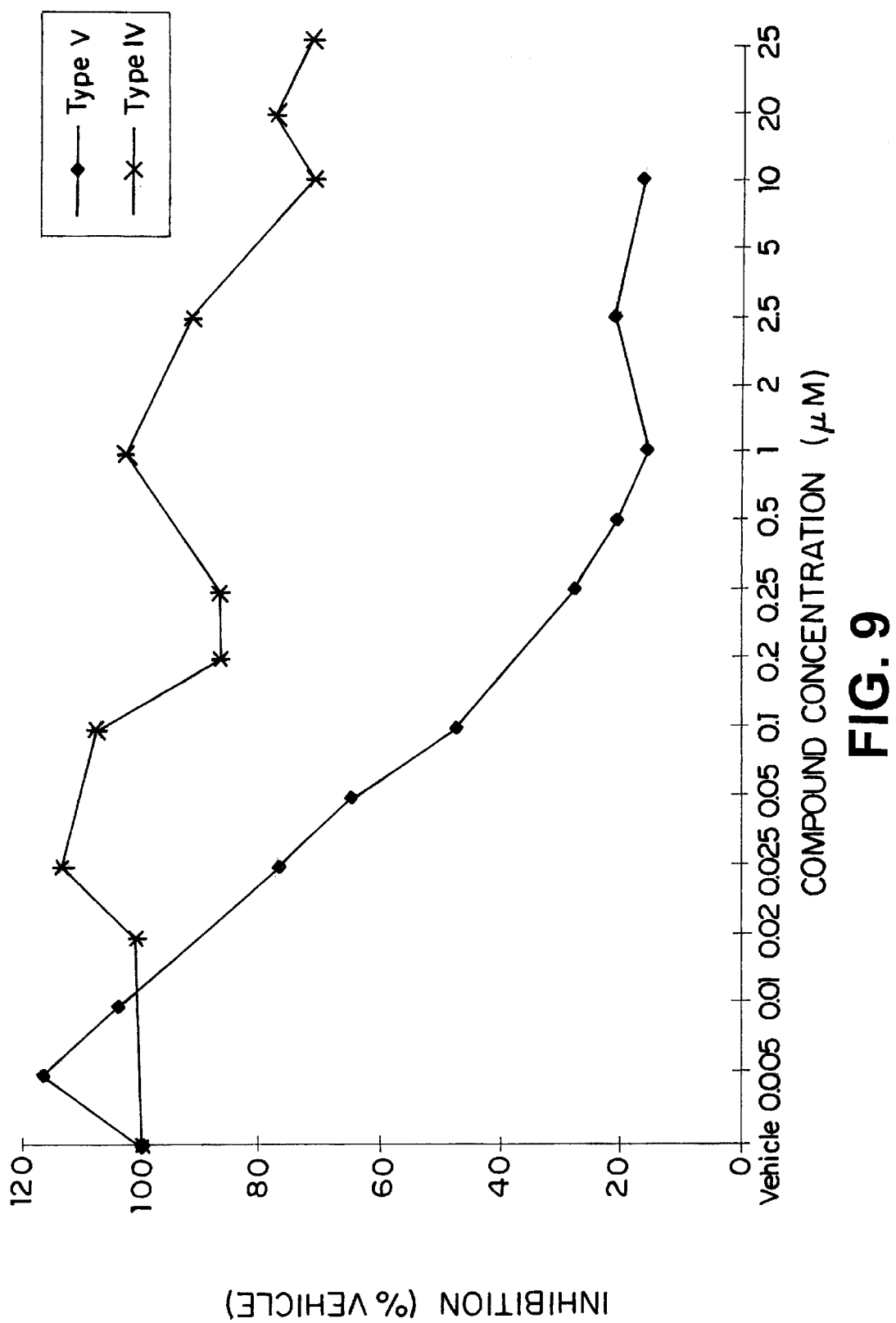
FIG. 9 illustrates the phosphodiesterase inhibitory activity of compound E.

FIG. 9 shows the effect of the indicated dose of test compound E on either PDE4 or cGMP PDE. The calculated $IC_{50}$ value was 0.08 $\mu$M for cGMP PDE and greater than 25 $\mu$M for PDE4.

TABLE 3 cGMP PDE inhibitory activity among a series of compounds

|  | % Inhibition at 10 $\mu$M |
|---|---|
| Reference compounds |  |
| Indomethacin | 34 |
| MY5445 | 86 |
| Sulindac sulfide | 97 |
| Exisulind | 39 |
| Test compounds |  |
| A | <25 |
| B | <25 |
| C | <25 |
| D | 36 |
| E | 75 |

The above compounds in Table 3 were evaluated for PDE inhibitory activity, as described in the protocol supra. Of the compounds that did not inhibit COX, only compound E was found to cause greater than 50% inhibition at 10 $\mu$M. As noted in FIG. 8, compound B showed inhibition of greater than 50% at a dose of 20 $\mu$M. Therefore, depending on the dosage level used in a single dose test, some compounds may be screened out that otherwise may be active at slightly higher dosages. The dosage used is subjective and may be lowered after active compounds are found at certain levels to identify even more potent compounds.

EXAMPLE 3

Apoptosis assay

Figure 10A:
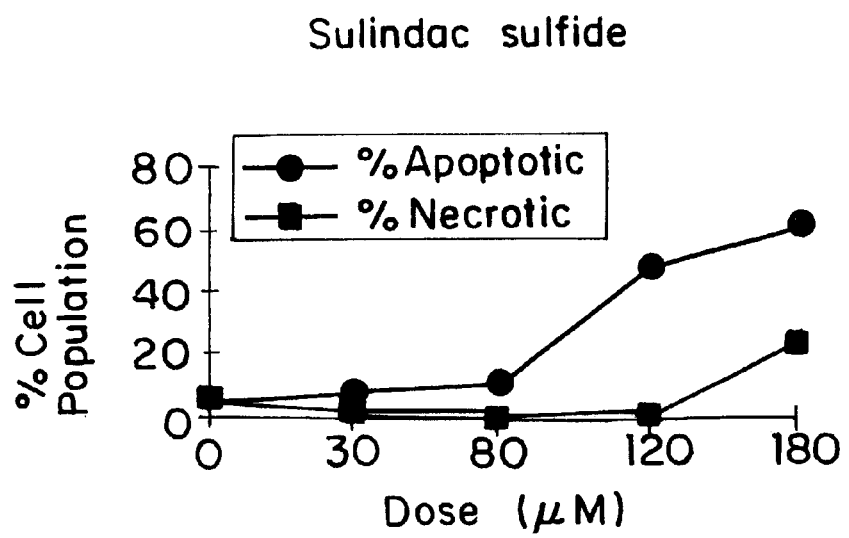
FIG. 10 illustrates the effects of sulindac sulfide and exisulind on apoptosis and necrosis of HT-29 cells.
Figure 10B:
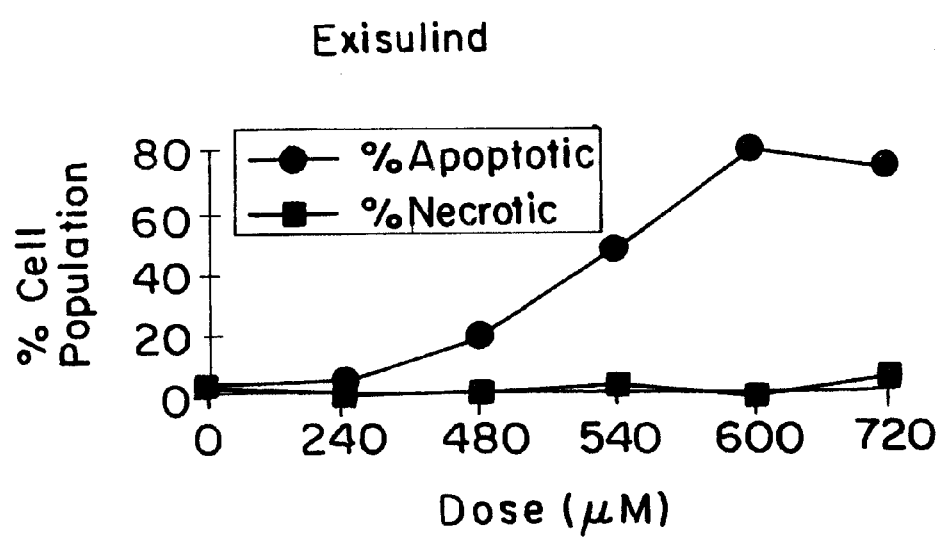

Reference compounds and test compounds were analyzed for their novel PDE inhibitory activity in accordance with the protocols for the assay, supra. In accordance with thos protocols, FIG. 10 shows the effects of sulindac sulfide and exisulind on apoptotic and necrotic cell death. HT-29 cells were treated for six days with the indicated dose of either sulindac sulfide or exisulind. Apoptotic and necrotic cell death was determined previously (Duke and Cohen, In: Current Protocols in Immunology, 3.17.1–3.17.16, New York, John Wiley and Sons, 1992). The data shows that both sulindac sulfide and exisulind are capable of causing apoptotic cell death without inducing necrosis. All data were collected from the same experiment.

Figure 11A:
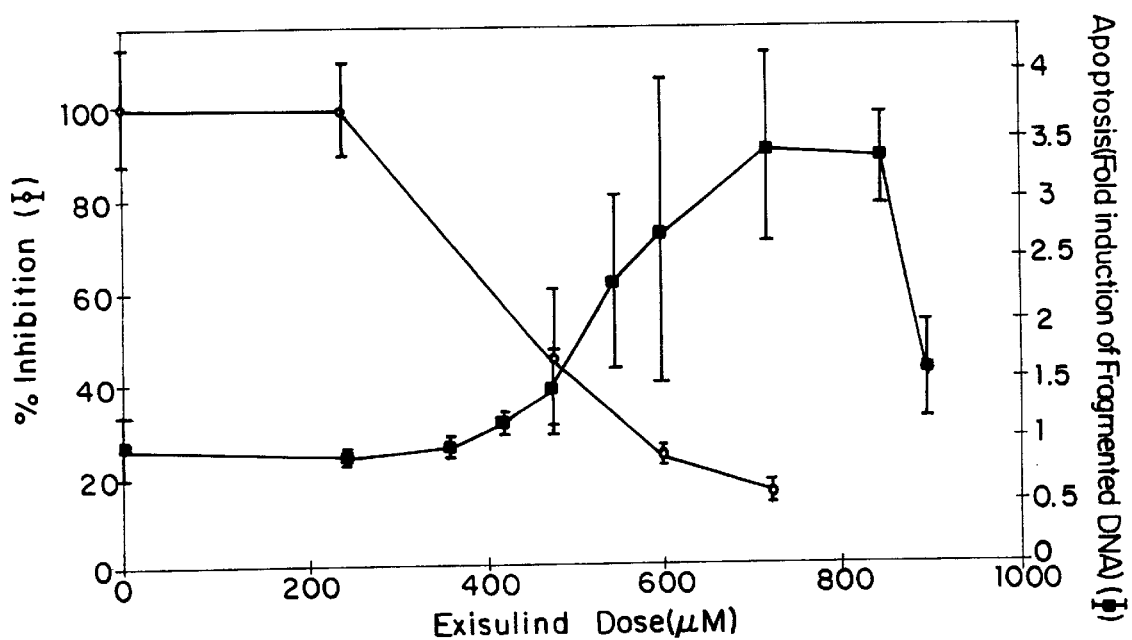
FIG. 11 illustrates the effects of sulindac sulfide and exisulind on HT-29 cell growth inhibition and apoptosis induction as determined by DNA fragmentation.
Figure 11B:
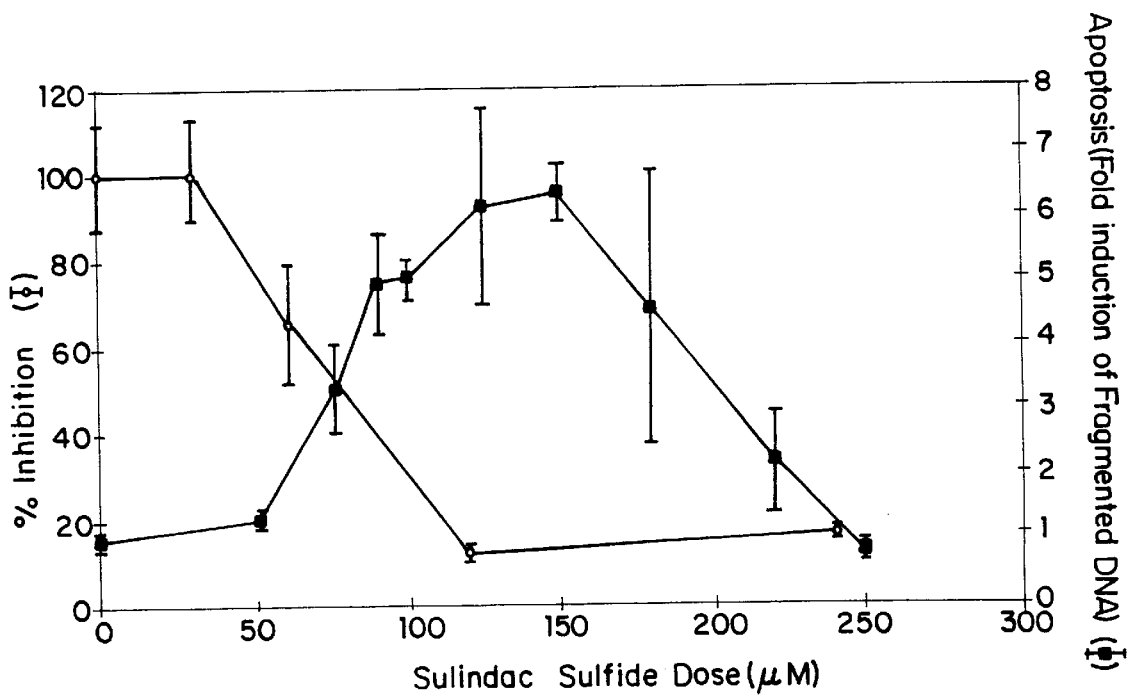

FIG. 11 shows the effect of sulindac sulfide and exisulind on tumor growth inhibition and apoptosis induction as determined by DNA fragmentation. Top figure (11A); growth inhibition (open symbols, left axis) and DNA fragmentation (closed symbols, right axis) by exisulind. Bottom figure (11B); growth inhibition (open symbols) and DNA fragmentation (closed symbols) by sulindac sulfide. Growth inhibition was determined by the SRB assay after six days of treatment. DNA fragmentation was determined after 48 hours of treatment. All data was collected from the same experiment.

Figure 12:
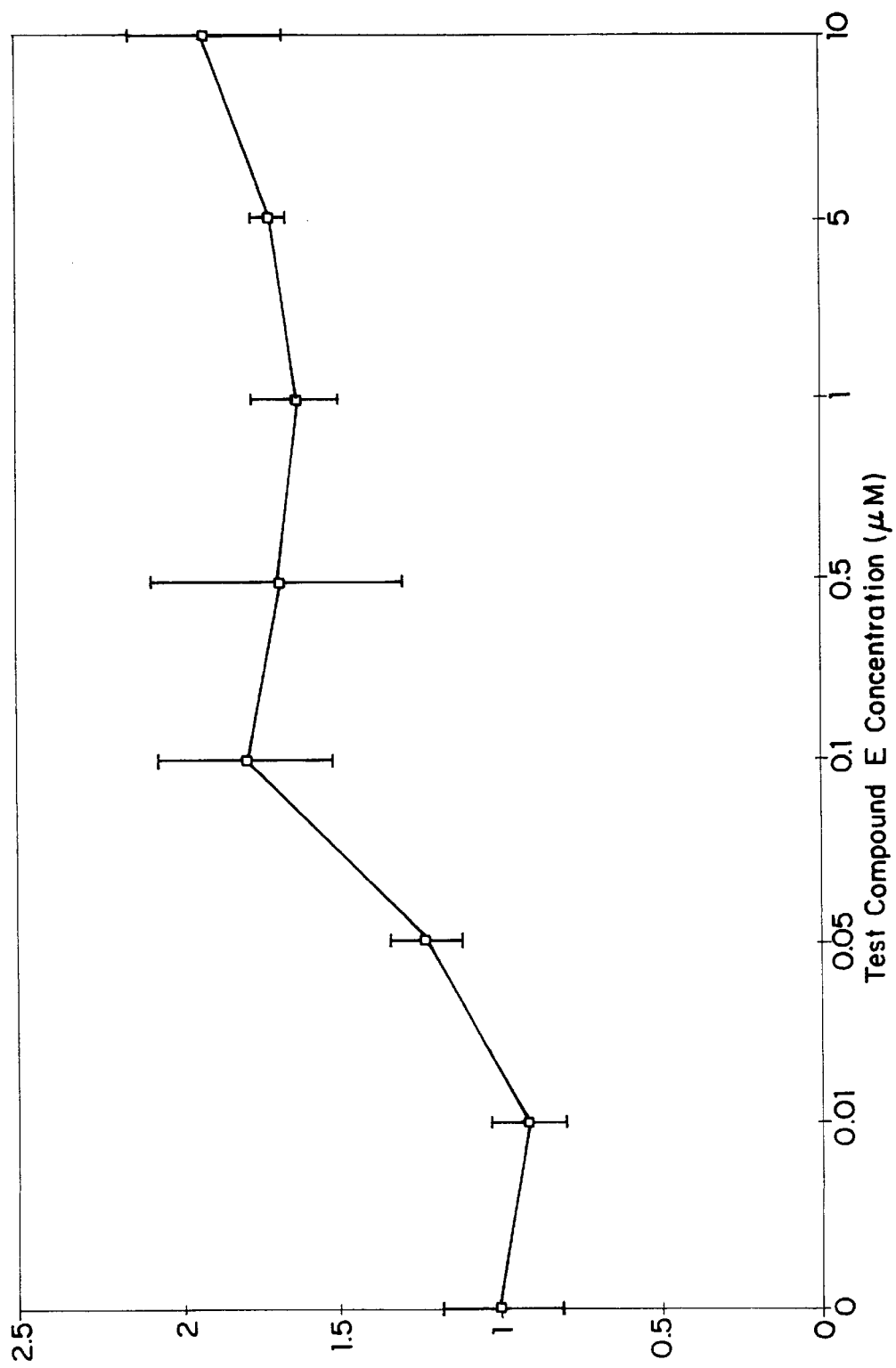
FIG. 12 illustrates the apoptosis inducing properties of compound E.

FIG. 12 shows the apoptosis inducing properties of compound E. HT-29 colon adenocarcinoma cells were treated with the indicated concentration of compound E for 48 hours and apoptosis was determined by the DNA fragmentation assay. The calculated $EC_{50}$ value was 0.05 μM.

Figure 13:
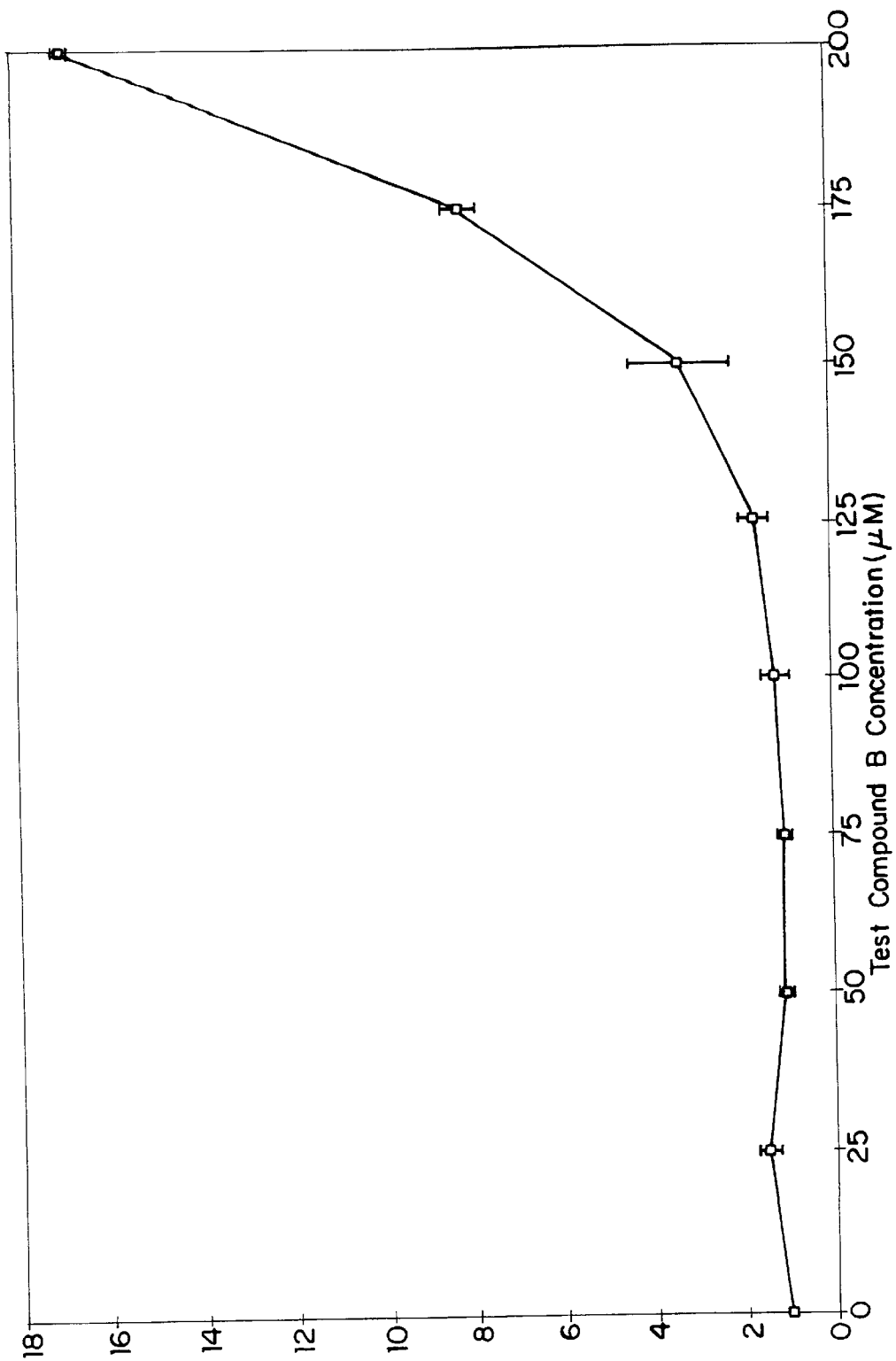
FIG. 13 illustrates the apoptosis inducing properties of compound B.

FIG. 13 shows the apoptosis inducing properties of compound B. HT-29 colon adenocarcinoma cells were treated with the indicated concentration of compound B for 48 hours and apoptosis was determined by the DNA fragmentation assay. The calculated $EC_{50}$ value was approximately 175 μM.

TABLE 4

Apoptosis inducing activity among a series of compounds

| | Fold induction at 100 μM |
|---|---|
| Reference compounds | |
| Indomethacin | <2.0 |
| MY5445 | 4.7 |
| Sulindac sulfide | 7.9 |
| Exisulind | <2.0 |
| E4021 | <2.0 |
| Zaprinast | <2.0 |
| Sildenafil | <2.0 |
| EHNA | <2.0 |
| Test compounds | |
| A | <2.0 |
| B | 3.4 |
| C | 5.6 |
| D | <2.0 |
| E | 4.6 |

In accordance with the fold induction protocol, supra, the compounds A through E were tested for apoptosis inducing activity, as reported in Table 4 above. Compounds B, C and E showed significant apoptotic inducing activity, greater than 2.0 fold, at a dosage of 100 μM. Of these three compounds, at this dosage only B and E did not inhibit COX but did inhibit cGMP-specific PDE.

The apoptosis inducing activity for a series of phosphodiesterase inhibitors was determined. The data are shown in Table 5 below. HT-29 cell were treated for 6 days with various inhibitors of phosphodiesterase. Apoptosis and necrosis were determined morphologically after acridine orange and ethidium bromide labelling in accordance with the assay described, supra. The data show that the novel cGMP-specific PDE is useful for screening compounds that induce apoptosis of HT-29 cells.

TABLE 5

Apoptosis-Induction Data for PDE Inhibitors

| Inhibitor | Reported Selectivity | % Apoptosis | % Necrosis |
|---|---|---|---|
| Vehicle | | 8 | 6 |
| 8-methoxy-IBMX | PDE1 | 2 | 1 |
| Milrinone | PDE3 | 18 | 0 |
| RO-20-1724 | PDE4 | 11 | 2 |
| MY5445 | PDE5 | 80 | 5 |
| IBMX | Non-selective | 4 | 13 |

EXAMPLE 4

Growth inhibition assay

Figure 14:
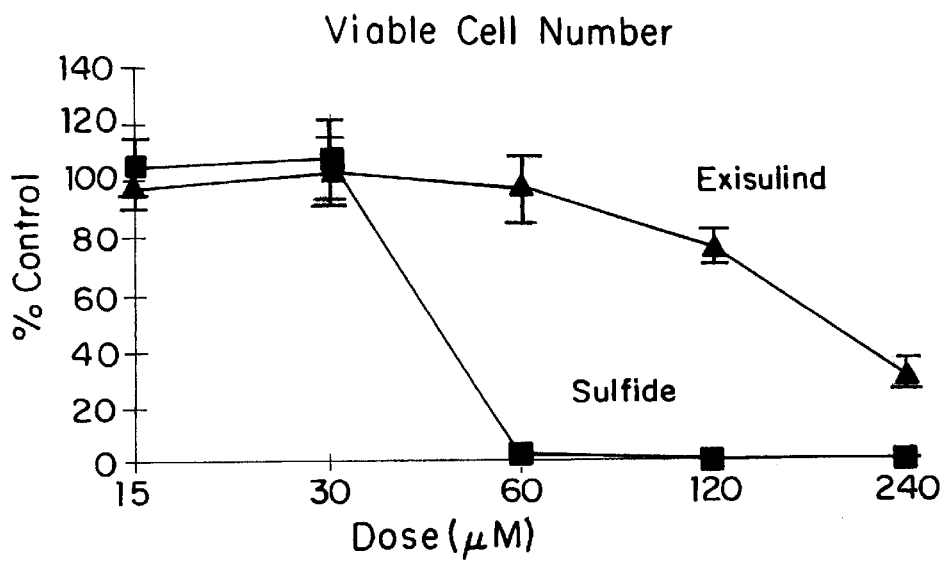
FIG. 14 illustrates the effects of sulindac sulfide and exisulind on tumor cell growth.

Reference compounds and test compounds were analyzed for their PDE5 inhibitory activity in accordance with the protocol for the assay supra. FIG. 14 shows the inhibitory effect of various concentrations of sulindac sulfide and exisulind on the growth of HT-29 cells. HT-29 cells were treated for six days with various doses of exisulind (triangles) or sulindac sulfide (squares) as indicated. Cell number was measured by a sulforhodamine assay as previously described (Piazza et al., Cancer Research, 55: 3110–3116, 1995). The $IC_{50}$ value for sulindac sulfide was approximately 45 μM and 200 μM for the exisulind. The data show that both sulindac sulfide and exisulind are capable of inhibiting tumor cell growth.

Figure 15A:
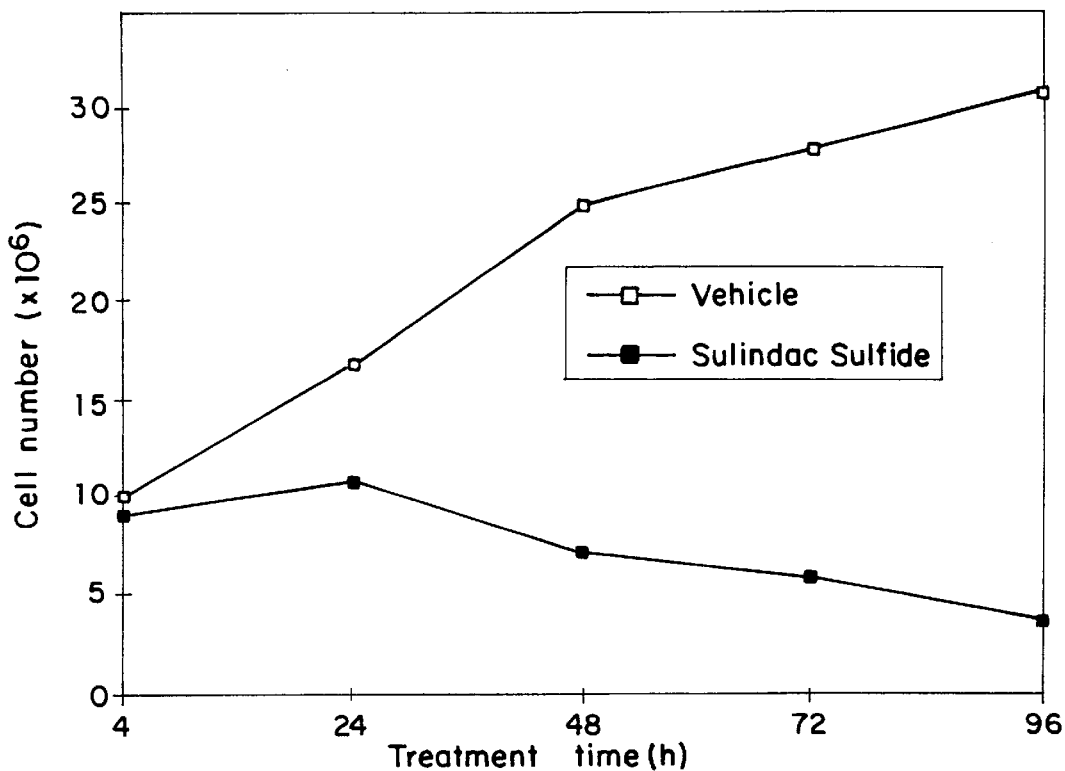
FIG. 15 illustrates the growth inhibitory and apoptosis-inducing activity of sulindac sulfide and control (DMSO).
Figure 15B:
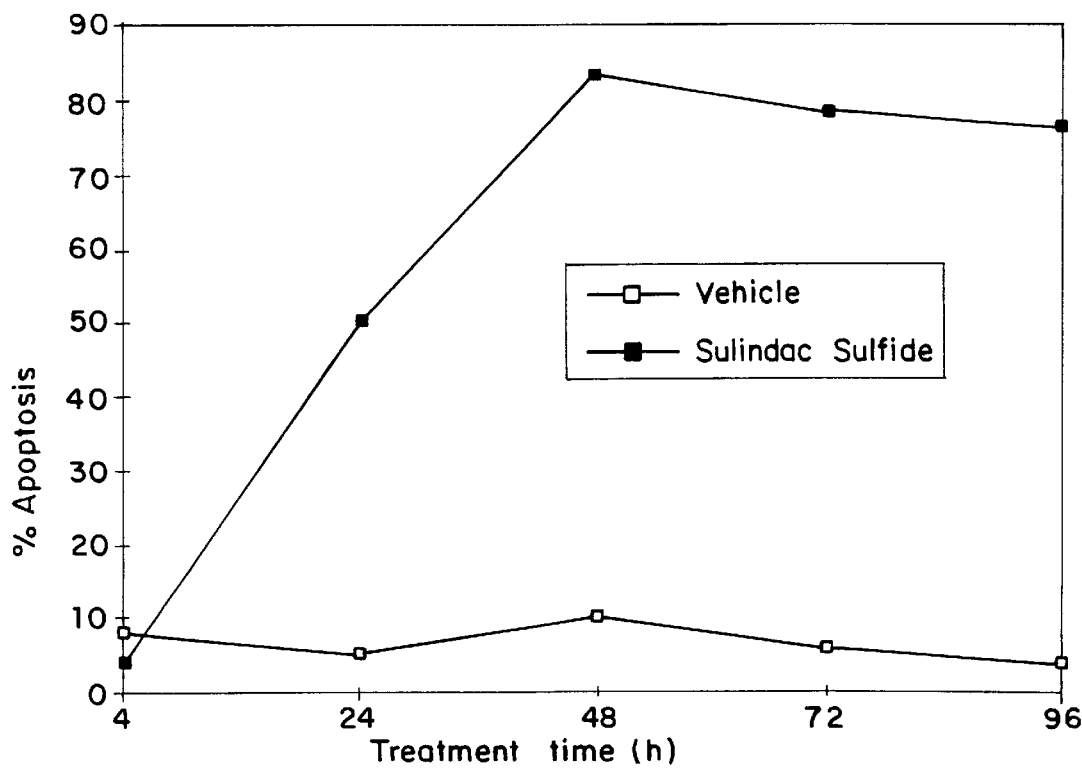

FIG. 15 shows the growth inhibitory and apoptosis-inducing activity of sulindac sulfide. A time course experiment is shown involving HT-29 cells treated with either vehicle, 0.1% DMSO (open symbols) or sulindac sulfide, 120 μM (closed symbols). Growth inhibition (15A top) was measured by counting viable cells after trypan blue staining. Apoptosis (15B bottom) was measured by morphological determination following staining with acridine orange and ethidium bromide as described previously (Duke and Cohen, In: Current Protocols in Immunology, 3.17.1–3.17.16, New York, John Wiley and Sons, 1992). The data demonstrate that sulindac sulfide is capable of inhibiting tumor cell growth and that the effect is accompanied by an increase in apoptosis. All data were collected from the same experiment.

Figure 16:
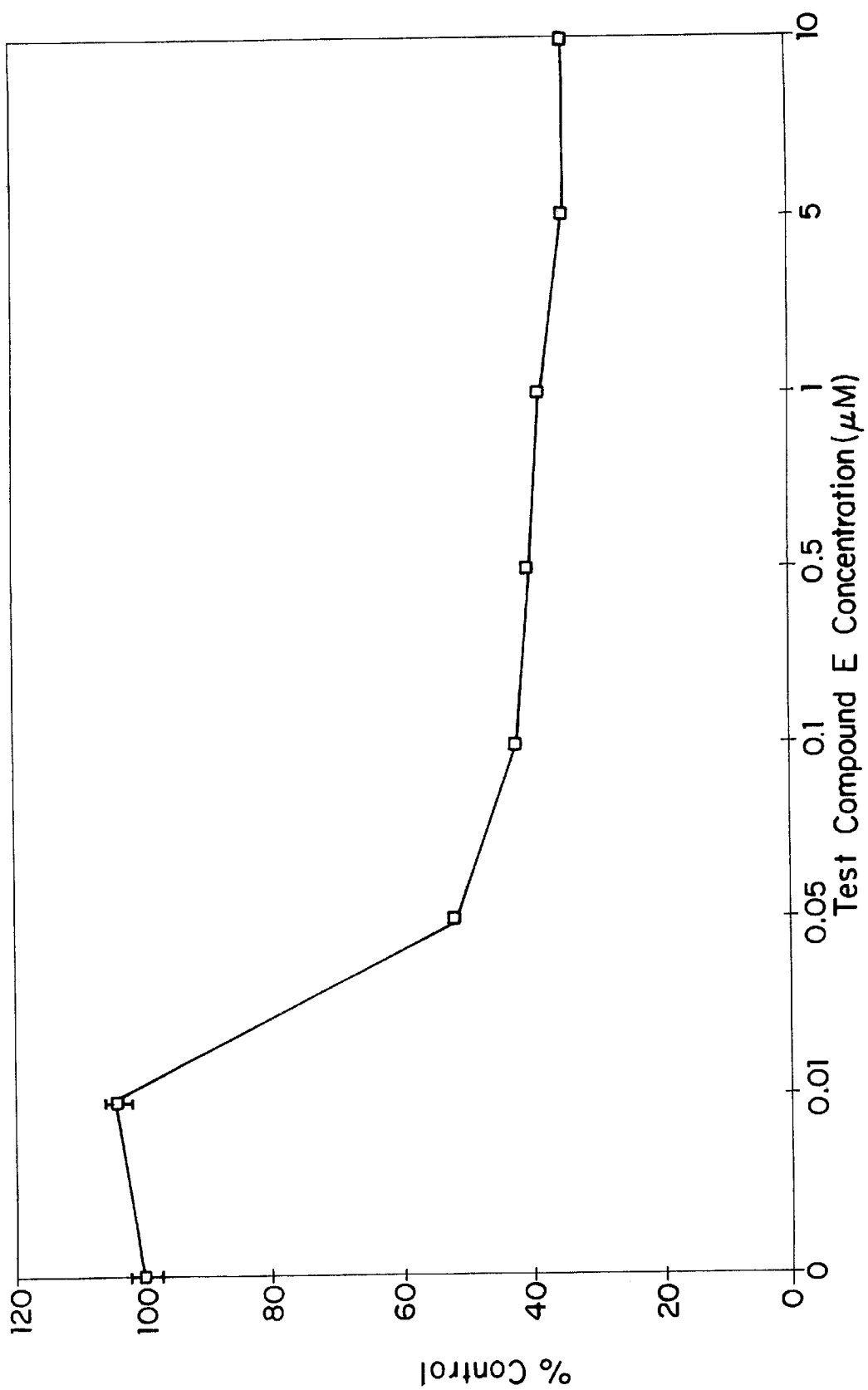
FIG. 16 illustrates the growth inhibitory activity of compound E.

FIG. 16 shows the growth inhibitory activity of test compound E. HT-29 colon adenocarcinoma cells were treated with the indicated concentration of comound E for six days and cell number was determined by the SRB assay. The calculated $IC_{50}$ value was 0.04 μM.

TABLE 6

Growth inhibitory activity among a series of compounds

| | % Inhibition at 100 μM |
|---|---|
| Reference compounds | |
| Indomethacin | 75 |
| MY5445 | 88 |
| Sulindac sulfide | 88 |
| Exisulind | <50 |
| E4021 | <50 |
| sildenafil | <50 |
| zaprinast | <50 |

TABLE 6-continued

Growth inhibitory activity among a series of compounds

| Test compounds | % Inhibition at 100 μM |
|---|---|
| A | 68 |
| B | 77 |
| C | 80 |
| D | 78 |
| E | 62 |

In accordance with the screening protocol of section supra, compounds A through E were tested for growth inhibitory activity, as reported in Table 6 above. All the test compounds showed activity exceeding the benchmark exisulind at a 100 μM single dose test.

The growth inhibitory activity for a series of phosphodiesterase inhibitors was determined. The data are shown in Table 7 below. HT-29 cell were treated for 6 days with various inhibitors of phospohodiesterase. Cell growth was determined by the SRB assay described, supra. The data below taken with those above show that inhibitors of the novel PDE were effective for inhibiting tumor cell growth.

TABLE 7

Growth Inhibitory Data for PDE Inhibitors

| Inhibitor | Reported Selectivity | Growth inhibition (IC$_{50}$, μM) |
|---|---|---|
| 8-methoxy-IBMX | PDE1 | >200 μM |
| Milrinone | PDE3 | >200 μM |
| RO-20-1724 | PDE4 | >200 μM |
| MY5445 | PDE5 | 5 μM |
| IBMX | Non-selective | >100 μM |
| Zaprinast | PDE5 | >100 μM |
| Sildenafil | PDE5 | >100 μM |
| E4021 | PDE5 | >100 μM |

To show the effectiveness of this screening method on various forms of neoplasia, compounds were tested on numerous cell lines. The effects of sulindac sulfide and exisulind on various cell lines was determined. The data are shown in table 8 below. The IC$_{50}$ values were determined by the SRB assay. The data show the broad effectiveness of these compounds on a broad range of neoplasias, with effectiveness at comparable dose range. Therefore, compounds identified by this invention should be useful for treating multiple forms of neoplasia.

TABLE 8

Growth Inhibitory Data of Various Cell Lines

| Cell Type/ Tissue specificity | IC$_{50}$(μM) | | |
|---|---|---|---|
| | Sulindac sulfide | Exisulind | Compound E* |
| HT-29, Colon | 60 | 120 | 0.10 |
| HCT116, Colon | 45 | 90 | |
| MCF7/S, Breast | 30 | 90 | |
| UACC375, Melanoma | 50 | 100 | |
| A-427, Lung | 90 | 130 | |
| Bronchial Epithelial Cells | 30 | 90 | |
| NRK, Kidney (non ras-transformed) | 50 | 180 | |
| KNRK, Kidney (ras transformed) | 60 | 240 | |
| Human Prostate Carcinoma PC3 | | 82 | 0.90 |
| Colo 205 | | | 1.62 |
| DU-145 | | | 0.10 |
| HCT-15 | | | 0.60 |
| MDA-MB-231 | | | 0.08 |
| MDA-MB-435 | | | 0.04 |

*Determined by neutral red assay as described by Schmid et al., in Proc. AACR Vol 39, p. 195 (1998).

EXAMPLE 5

Activity in mammary gland organ culture model

Figure 17:
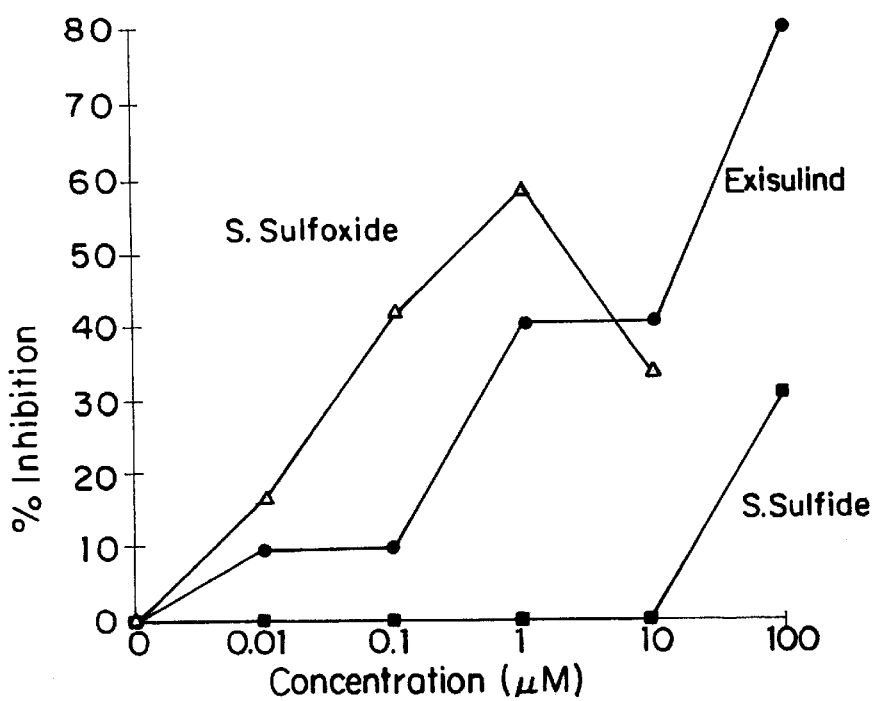
FIG. 17 illustrates the inhibition of pre-malignant, neoplastic lesions in mouse mammary gland organ culture by sulindac metabolites.

FIG. 17 shows the inhibition of premalignant lesions in mammary gland organ culture by sulindac metabolites. Mammary gland organ culture experiment were performed as previously described (Mehta and Moon, *Cancer Research*, 46: 5832–5835, (1986). The results demonstrate that sulindac and exisulind effectively inhibit the formation of premalignant lesions, while sulindac sulfide was inactive. The data support the hypothesis that cyclooxygenase inhibition is not necessary for the anti-neoplastic properties of desired compounds.

ANALYSIS

To identify compounds that have potential use for treating neoplasia, this invention provides a rationale for comparing experimental data of test compounds from several protocols. Within the framework of this invention, test compounds can be ranked according to their potential use for treating neoplasia in humans. Those compounds having desirable effects may be selected for more expensive and time consuming animal studies that are required to get approval before initiating human clinical trials.

Qualitative data of various test compounds and the several protocols are shown in Table 9 below. The data show that exisulind, compound B and compound E exhibit the appropriate activity to pass the screen of four assays: lack of COX inhibition, and presence of effective cGMP-specific PDE inhibition, growth inhibition and apoptosis induction. The activity of these compounds in the mammary gland organ culture validates the effectiveness of this invention. The qualitative valuations of the screening protocols rank compound E best, then compound B and then exisulind.

TABLE 9

Activity Profile of Various Compounds

| Compound | COX Inhibition | PDE Inhibition | Growth Inhibition | Apoptosis | Mammary Gland Organ Culture |
|---|---|---|---|---|---|
| Exisulind | − | ++ | ++ | ++ | +++ |
| Sulindac sulfide | ++++ | +++ | +++ | +++ | − |
| MY5445 | ++++ | +++ | +++ | +++ | + |

TABLE 9-continued

Activity Profile of Various Compounds

| Compound | COX Inhibition | PDE Inhibition | Growth Inhibition | Apoptosis | Mammary Gland Organ Culture |
|---|---|---|---|---|---|
| A | − | − | +++ | ++ | ++ |
| B | − | +++ | +++ | +++ | ++ |
| D | − | − | ++ | − | − |
| E | − | ++++ | ++++ | ++++ | ++++ |
| F | − | − | ++ | + | − |
| G | − | − | +++ | ++ | +++ |
| H | − | − | ++ | − | − |

Table 9 Code: Activity of compounds based on evaluating a series of experiments involving tests for maximal activity and potency.
−Not active
+Slightly active
++Moderately active
+++Strongly active
++++Highly active Obviously, numerous modifications and variations of the present invention are possible in light of the above teachings. It is therefore to be understood that within the scope of the appended claims, the invention may be practiced otherwise than as specifically described herein.

We claim:

1. A method for identifying a compound with potential for treating neoplasia, comprising
   determining cyclooxygenase (COX) inhibitory activity of the compound; and
   determining phospodiesterase ("PDE") inhibition activity of the compound wherein said PDE is characterized by
   (a) a greater specificity for cGMP than cAMP;
   (b) positive cooperative kinetic behavior in the presence of cGMP substrate;
   (c) submicromolar affinity for cGMP; and
   (d) insensitivity to phosphorylation by cGMP-dependent protein kinase
   wherein low COX inhibitory activity and high PDE inhibition activity identifies that the compound has potential for treating neoplasia.

2. The method of claim 1, further comprising determining whether the compound inhibits tumor cell growth in a culture;
   wherein inhibition of tumor cell growth is further identifies that the compound has potential for treating neoplasia.

3. The method of claim 1, further comprising
   determining whether the compound induces apoptosis of a tumor cell;
   wherein induction of apoptosis is further identifies that the compound has potential for treating neoplasia.

4. The method of claim 3, further comprising
   determining whether the compound inhibits tumor cell growth in a sample;
   wherein inhibition of tumor cell growth is further identifies that the compound is useful for treating neoplasia.

5. The method of claim 3, wherein said PDE inhibition activity is determined by:
   contacting the compound with a cell culture; and
   determining the intracellular cyclic GMP concentration;
   wherein said PDE inhibitory activity greater than 50% at a concentration of 10 $\mu$M idenitifies that a compound has potential for treating neoplasia.

6. The method of claim 3 further including:
   determining the ratio of intracellular cyclic GMP to cyclic AMP in neoplastic cells both before and after exposure of said cells to said compound wherein an increase in that ratio after exposure greater than three-fold as compared to before exposure identifies that a compound has potential for treating neoplasia.

7. A method of selecting a compound for inhibition of neoplasia, comprising
   determining neoplastic cell growth inhibitory activity of the compound;
   determining phosphodiesterase ("PDE") inhibitory activity of the compound wherein said PDE is characterized by
   (a) a greater specificity for cGMP than cAMP;
   (b) positive cooperative kinetic behavior in the presence of cGMP substrate;
   (c) submicromolar affinity for cGMP; and
   (d) insensitivity to phosphorylation by cGMP-dependent protein kinase; and
   selecting the compound that exhibit neoplastic cell growth inhibitory activity and high PDE inhibition activity PDE as a compound to inhibit neoplasia.

8. The method of claim 7, further comprising
   selecting compounds where the $IC_{50}$ value for growth inhibitory activity is less than about 100 $\mu$M for potential use in treating neoplasia.

9. The method of claim 7, further comprising
   determining whether the compound induces apoptosis in a cell; and
   selecting compounds that induce apoptosis.

10. The method of claim 9, further comprising
    selecting compounds where the $EC_{50}$ value for apoptotic activity is less than about 100 $\mu$M.

11. A method for identifying compounds for tretment of neoplasia, comprising the steps of:
    determining COX inhibitory activity of the compounds;
    determining phosphodiesterase ("PDE") inhibition activity of the compounds wherein said PDE is characterized by
    (a) a greater specificity for cGMP than cAMP;
    (b) positive cooperative kinetic behavior in the presence of cGMP substrate;
    (c) submicromolar affinity for cGMP;
    (d) insensitivity to phosphorylation by cGMP-dependent protein kinase;
    (e) insensitivity to inhibition by zaprinast; and
    identifying those compounds for treating neoplasia in patients if said compounds exhibit low COX inhibitory activity and high PDE inhibition activity.

12. The method of claim 11 further comprising determining growth inhibitory activity of the compounds; and identifying those compounds with phosphodiesterase inhibitory activity substantially greater than COX inhibitory activity at concentrations exhibiting substantial growth inhibitory activity.

13. A method for screening a compound with potential for treating neoplasia comprising determining phosphodiesterase ("PDE") inhibition activity of said compound wherein said PDE is characterized by
    (a) a greater specificity for cGMP than cAMP;
    (b) positive cooperative kinetic behavior in the presence of cGMP substrate;
    (c) submicromolar affinity for cGMP; and
    (d) insensitivity to phosphorylation by cGMP-dependent protein kinase; wherein a compound with high PDE inhibition activity has potential for treating neoplasia.

* * * * *